United States Patent
Lazo et al.

[11] Patent Number: 5,925,660
[45] Date of Patent: *Jul. 20, 1999

[54] PHOSPHATASE INHIBITORS AND METHODS OF USE THEREOF

[75] Inventors: John S. Lazo, Pittsburgh; Robert L. Rice, Glenshaw; April Cunningham, Harleysville; Peter Wipf, Pittsburgh, all of Pa.

[73] Assignee: University of Pittsburgh, Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/917,016

[22] Filed: Aug. 22, 1997

Related U.S. Application Data

[62] Division of application No. 08/688,530, Jul. 30, 1996, Pat. No. 5,700,821.

[51] Int. Cl.⁶ .......................... A61K 31/42; A61K 31/47; A61K 31/445; A61K 31/44; A61K 31/495
[52] U.S. Cl. .......................... 514/374; 514/313; 514/314; 514/326; 514/340; 514/255
[58] Field of Search ..................... 514/374, 313, 514/314, 326, 340, 255

[56] References Cited

U.S. PATENT DOCUMENTS

| | | | |
|---|---|---|---|
| 5,280,034 | 1/1994 | Hall et al. | 514/374 |
| 5,583,232 | 12/1996 | Kempf et al. | 548/204 |
| 5,733,876 | 3/1998 | O'Reilly et al. | 514/12 |
| 5,770,620 | 6/1998 | Mjalli et al. | 514/415 |

OTHER PUBLICATIONS

Honkanan et al. (1994) *Toxicon* 32 : 339.
MacKintosh et al. (1995) *FEBS Letters* 371 : 236.
Murray et al. (1994) *Annual Reports in Medicinal Chemistry* 29: 255.
Nishiwaki et al. (1990) *Carcinogenesis* 11 : 1837.
Quinn et al. (1993) *Bioorganic and Medicinal Chemistry Letters* 3 : 1029.
Sugiyama et al (1995) *Bioiorganic and Medicinal Chemistry Letters* 6 :3.
Takai et al. (1992) *Biochem. J.* 284:539.
Taylor et al. (1992) *Bioorganic and Medicinal Chemistry Letters* 2 : 299.
Thompson et al. (1996) *Chem. Rev.* 96 : 555.

*Primary Examiner*—Jerome D. Goldberg
*Attorney, Agent, or Firm*—Baker & Botts

[57] ABSTRACT

The present invention is directed to compounds having the formula:

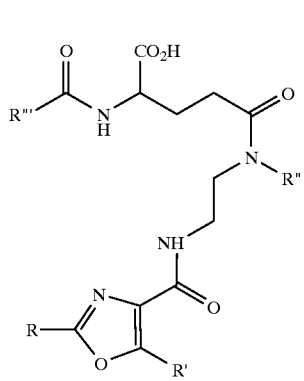

The invention further provides a method of making the compounds. The compounds are useful as inhibitors of protein phosphatases, for example PP1, PP2A, PP3, CDC25A and CDC25B. The invention is further directed to a method of inhibiting a protein phosphatase, a method of inhibiting cell proliferation, and pharmaceutical compositions comprising the subject compounds.

5 Claims, 7 Drawing Sheets

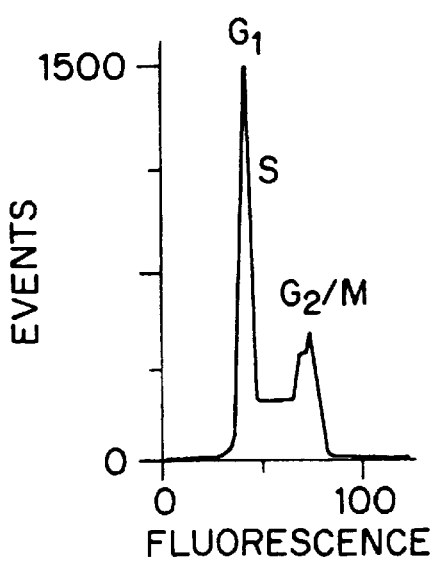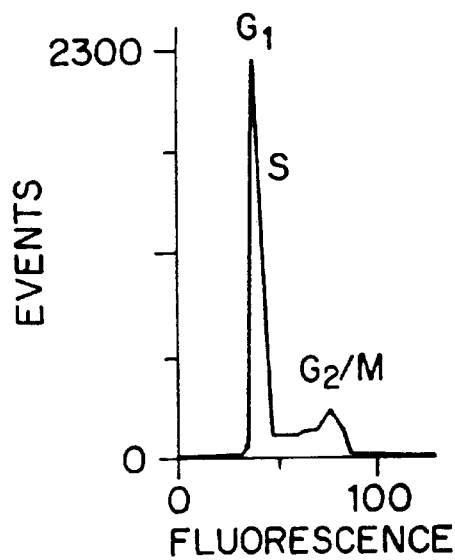
FIG. 10A  FIG. 10B
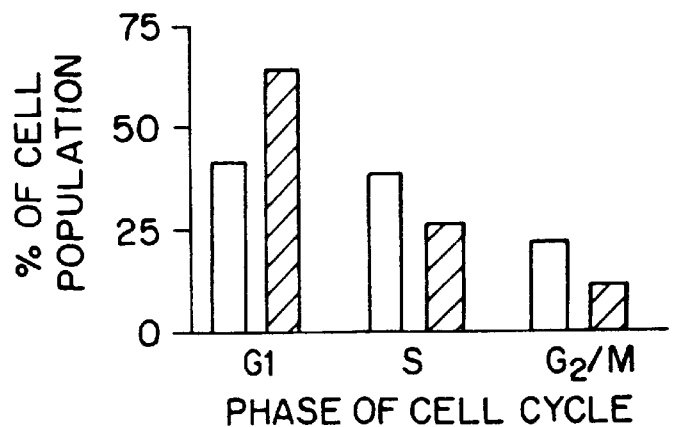
FIG. 10C
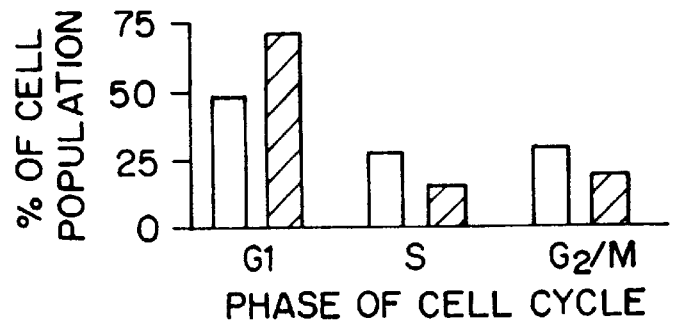
FIG. 10D

PHOSPHATASE INHIBITORS AND METHODS OF USE THEREOF

This is a divisional of application Ser. No. 08/688,530 filed on Jul. 30, 1996 now U.S. Pat. No. 5,700,821.

FIELD OF THE INVENTION

The regulation of protein phosphorylation by kinases and phosphatases controls many eukaryotic cell functions, including signal transduction, cell adhesion, gene transcription and cell proliferation. The identification and characterization of kinases, phosphatases, and inhibitors thereof thus allows pharmaceutical regulation of a variety of cellular functions. The present invention provides inhibitors of protein phosphatases, and methods of making and using the inhibitors. The compounds of the present invention are useful, for example, as inhibitors of cell proliferation.

BACKGROUND OF THE INVENTION

Many eukaryotic cell functions, including signal transduction, cell adhesion, gene transcription, RNA splicing, apoptosis and cell proliferation, are controlled by protein phosphorylation. Protein phosphorylation is in turn regulated by the dynamic relationship between kinases and phosphatases. Considerable research in synthetic chemistry has focused on protein kinases. However, recent biological evidence for multiple regulatory functions of protein phosphatases has triggered further investigation of phosphatases. The protein phosphatases represent unique and attractive targets for small-molecule inhibition and pharmacological intervention.

Most eukaryotic amino acid phosphate derivatives in polypeptides and proteins are found on serine, threonine and tyrosine residues. Three basic types of eukaryotic protein phosphatases have been defined: serine/threonine protein phosphatases (PSTPases), tyrosine protein phosphatases (PTPases), and dual-specificity phosphatases (DSPases). The DSPases dephosphorylate tyrosine and threonine residues on the same polypeptide substrate.

The serine/threonine protein phosphatases (PSTPases) are further classified into subfamilies (PP1, PP2A, PP2B, PP2C and PP3) by substrate specificity, metal ion dependence and sensitivity to inhibition. At least forty different enzymes of this type have been identified through DNA cloning. Potent inhibitors of the serine/threonine phosphatases have been identified, including proteins designated Inhibitor-1, Inhibitor-2, DARPP-32, and NIPP-1, which are reviewed for example by Honkanen et al. in *Protein Kinase C*, Kuo, ed., Oxford Univ. Press, Oxford, 1994, p.305. In addition, several toxins, mostly from marine organisms, have been identified as potent inhibitors of the serine/threonine phosphatases. The natural product inhibitors are depicted in FIG. 1 and discussed for example by Fujiki et al. (1993) *Gazz. Chim. Ital.* 123: 309.

Okadaic acid, a polyether fatty acid produced by several species of marine dinoflagellates, reversibly inhibits the catalytic subunits of serine/threonine phosphatase subtypes PP1, PP2A and PP3. However, okadaic acid does not rapidly penetrate cell membranes and accumulates within cells slowly, making it difficult to control the intracellular concentration of the compound. Further, okadaic acid is not very chemically stable.

Other natural product inhibitors have been identified that are more stable, may penetrate some cell types better, are more potent, and exhibit selectivity toward different PSTPase isotypes. Calyculin A is a cytotoxic component of the marine sponge *Discodermia calyx*. It has an extremely high affinity to PP1, PP2A and PP3, with an inhibitory concentrations$_{50}$ ($IC_{50}$, the concentration that causes 50% inhibition compared to untreated control preparation) being about 0.3 nM. Microcystins are potent cyclic hepta- and pentapeptide toxins of the general structure cyclo[D-Ala-X-D-erythro-b-methyl-iso-Asp-Y-Adda-D-iso-Glu-N-methyldehydro-Ala] wherein X and Y are variable L-amino acids. Microcystins are known to promote tumors in vivo, but, with the exception of hepatocytes, are impermeable to most cells in vitro. Compounds of the nodularin series exhibit $IC_{50}$'s for PP1 and PP3 of about 2 and 1 nM, respectively. Motuporin, which has been recently isolated from a New Guinea sponge, is even more potent, with an $IC_{50}$ of less than 1 nM for PP1. Tautomycin is produced by a terrestrial Streptomyces strain, and inhibits PP1, PP2A and PP3 indiscriminately with an $IC_{50}$ in the 15 nM range. The remaining natural product inhibitors, thyrsiferal-23-acetate acetate and cantharidine, are somewhat selective, but weak ($IC_{50}$ of 0.16–10 $\mu$M), inhibitors of PP2A.

High toxicity, especially hepatotoxicity, is commonly found with the naturally occurring serine/threonine phosphatase inhibitors. The high toxicity appears to be intrinsically associated with non-specific phosphatase activity, and often limits the range of feasible pharmacological studies. Honkanen (1994) *Toxicon* 32: 339. Further, the chemical diversity of compounds obtained from natural sources is limited. Accordingly, there is a need in the art to diversify the chemical complexity of the natural products and to optimize biochemical and pharmacological effects.

However, only limited structure-activity relationship (SAR) studies have been reported on naturally occurring serine/threonine phosphatase inhibitors. For example, SAR studies of okadaic acid indicate that the carboxyl group as well as the four hydroxyl groups are important for activity. Nishiwki et al. (1990) *Carcinogenesis* 11:1837; Takai et al. (1992) *Biochem J.* 284:539; Sasaki et al. (1994) *Biochem J.* 288:259.

A limited SAR study of naturally occurring microcystins was performed by Rinehart et al. (1994) *J. Appl. Phycol.* 6: 159. It was found that the substitution of alanine for arginine has little effect on phosphatase inhibitory potency, but does result in a difference in relative cytotoxicity. The dehydroamino acid residue and the N-methyl substituents were also found to be noncritical. Esterification of the glutamic acid residue led to inactive compounds, and the (6Z) Adda isomer was inactive, suggesting the criticality of the glutamic acid unit and the overall shape of the Adda residue. However, some variations in the Adda unit, for example the O-demethyl and the O-demethyl-O-acetyl analogs, exerted little effect on bioactivity. The general SAR of the nodularin series appears similar to the microcystins, although fewer compounds are available for testing. SAR studies have not been reported to date for calyculin A, tautomycin or thyrsiferyl acetate.

The DSPase class of phosphatases has recently been defined, and its members are emerging as important regulators of cell cycle control and signal transduction. The first documented DSPase, VH1, as described by Guan et al. (1992) *Proc. Natl. Acad. Sci. USA* 89: 12175, corresponds to the H1 open reading frame of Vaccinia virus. Other members of the DSPase class have been identified and generally fall into two substrate motifs, the VH1 type and the CDC25 type. Mammalian cells contain at least three cdc25 homologues (cdc25A, cdc25B and cdc25C). The CDC25 phosphatases are positive regulators of cell cycle progression, and are reviewed by Hunter et al. (1994) *Cell*: 573. Further, there is a strong link between overexpression of the CDC25 phosphatases and oncogenic transformations, particularly in human breast cancer. Galaktinov et al.(1995) *Science* 269: 1575. However, no potent inhibitors of the DSPases are known.

Since nearly all forms of human neoplasias have altered cell cycle control, the role of phosphatases in cell cycle control makes these molecules attractive targets for pharmaceutical intervention. The ability of phosphatase inhibitors to interfere with aberrant cell activity has been demonstrated. For example, the naturally occurring PSTPase inhibitor okadaic acid has been shown to induce apoptosis in myeloid leukemia cells (Ishida et al.(1992) *J. Cell. Physiol.* 150: 484) and in rat hepatocytes, rat pituitary adenoma cell, human mammary carcinoma cells and human neuroblastoma cells (Boe et al.(1991) *Exp. Cell Res.* 195: 237). Thus there is a significant need to design and synthesize selective modulators of this family of enzymes in order to identify useful therapeutic agents.

SUMMARY OF THE INVENTION

The present invention provides a compound having the formula:

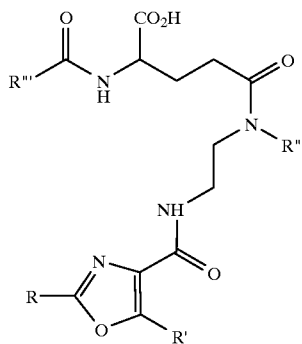

I wherein R, R', R" and R''' are the same or different and are preferably hydrophobic groups.

In another embodiment, the present invention provides a method of synthesizing a compound having the formula:

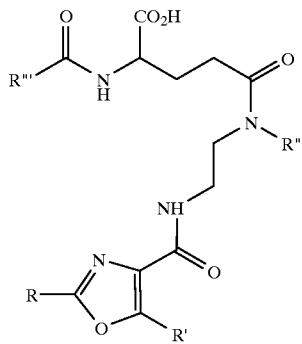

I wherein R, R', R" and R''' are the same or different and are preferably hydrophobic groups.

The method of synthesis comprises coupling glutamate to a solid support, adding the hydrophobic residue R''' COX, wherein X is a leaving group, adding diamine having the formula —NHCH$_2$CH$_2$NH(R"), adding oxazole carboxylic acid having the formula

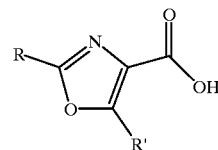

wherein R and R' are the same or different and are preferably hydrophobic groups, and cleaving the resulting compound from the solid support.

The present invention further provides a method of inhibiting a protein phosphatase comprising contacting a phosphatase-inhibiting effective amount of a compound of formula I with a protein phosphatase under conditions whereby the activity of the protein phosphatase is inhibited.

The present invention further provides a method of inhibiting cell proliferation comprising introducing into cells a proliferation-inhibiting amount of a compound of formula I. In a preferred embodiment the cells are human breast cancer cells.

Pharmaceutical compositions comprising a compound of formula I and a pharmaceutically acceptable carrier are also provided by the present invention.

BRIEF DESCRIPTION OF THE DRAWINGS

FIGS. 10A–D depict cell cycle distribution of human breast cancer cells after treatment with compound if determined by flow cytometry. FIG. 10A shows flow cytometry analysis of MDA-MB-231 cells treated with vehicle alone. FIG. 10B shows flow cytometry analysis 48 hours after treatment with 88 μM compound if. Fluorescence channel measures intracellular propidium iodide concentration, an index of DNA content. Horizontal bars are the gating positions that allow for cell cycle analysis. FIG. 10C shows MDA-MB-231 cell cycle distribution 48 hours after continuous treatment with 88 μM compound if, and is the result of one experiment. Open bars are control cells and black bars are cells treated with compound if. FIG. 10D shows cell cycle distribution 72 hours after continuous treatment with 88 µM compound if. The mean values were obtained from three independent determinations. Open bars are control cells and black bars are cells treated with 88 µM compound if. The standard errors of the means are displayed.

DETAILED DESCRIPTION OF THE INVENTION

Figure 1:
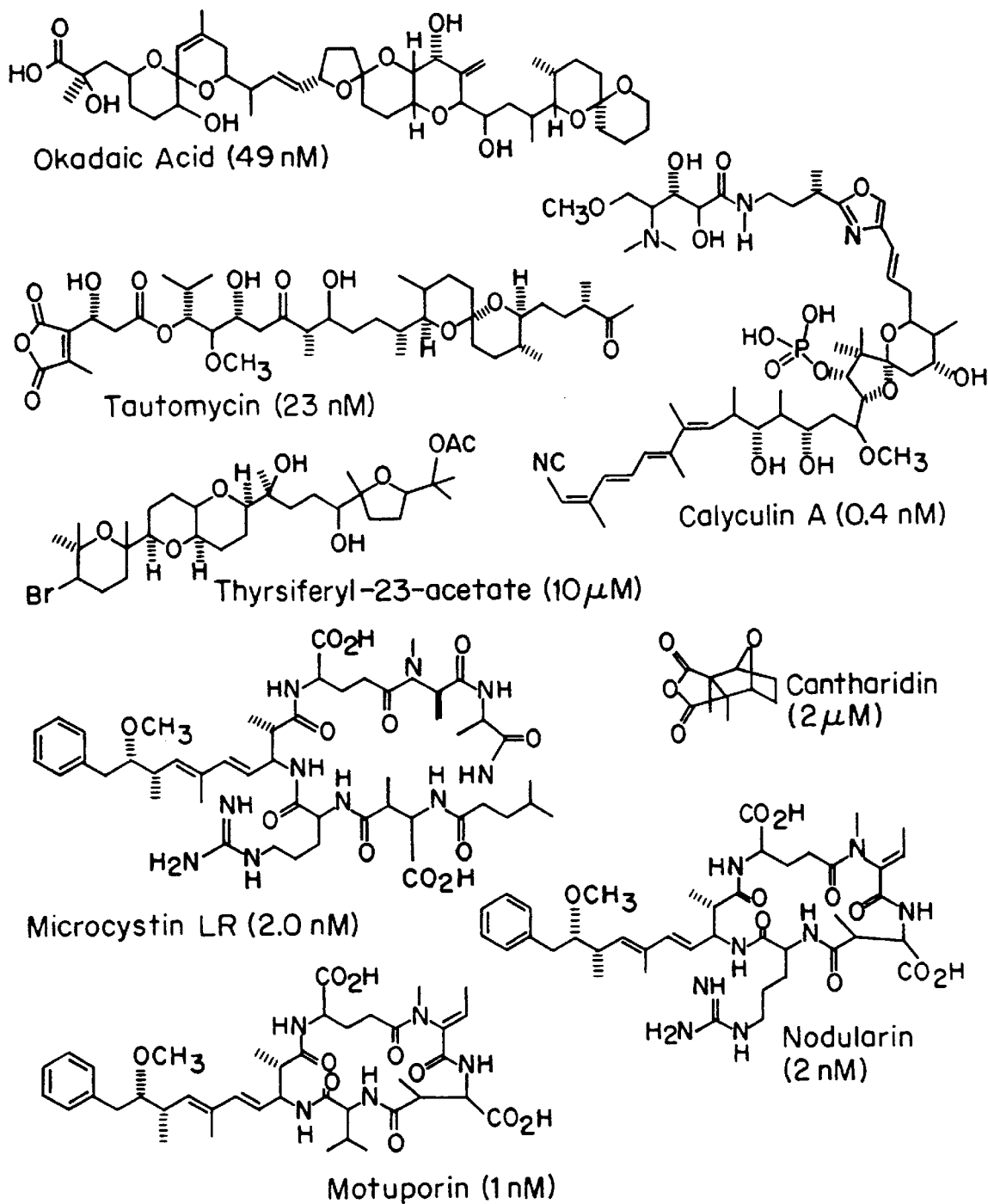
FIG. 1 depicts the formulae of naturally occurring inhibitors of the serine/threonine phosphatases.

The present invention provides compounds having the formula I as follows:

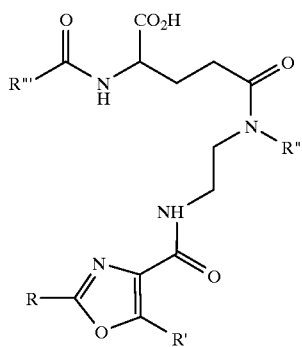

I wherein R, R', R" and R'" are the same or different and are preferably hydrophobic groups. In a preferred embodiment, R, R', R" and R'" are independently H, alkyl, alkenyl, alkynyl, cycloalkyl, phenyl (Ph), oxetanyl, azetidinyl, furanyl, pyrrole, indolyl, oxazolyl, isoxazolyl, imidazolyl, pyrazolyl, triazolyl, tetrazolyl, pyranyl, pyridyl, pyridonyl, piperidyl, piperazinyl, quinolyl, azepinyl, and diazepinyl. In another preferred embodiment, R and R'" are independently Ph, $CH_3$, n-$C_5H_{11}$, n-$C_7H_{15}$, n-$C_9H_{19}$, PhCHCH, $PhCH_2CH_2$, $Ph(CH_2)_2CC(CH_3)$, (p-MeO) Ph, (p-MeNHCO)Ph, $PhCHC(CH_3)CH_2CH_2$, $Ph(CH_2)_2$ $CHCHCHC(CH_3)$, $Ph(CH_2)_2CHCHCHCH$, $Ph(CH_2)_3CHC$ $(CH_3)CHCH$, $C_6H_{13}CH(CH_3)CHC(CH_3)CHCH$, or $C_4H_9CH(CH_3)CHC(CH_3)CHC(CH_3)$, R' is H, $CH_3$ or Ph, and R" is H, $CH_3$, benzyl (Bn), $CH_2CH(CH_3)$ n-$C_6H_{13}$, $CH_2CH_2NHBn$, $CH_2CH_2Ph$, or $(CH_2)_3Ph$. In a most preferred embodiment, R is Ph, R' is Ph, R" is Bn or $CH_3$ and R'" is n-$C_9H_{19}$.

The compounds of the present invention may be synthesized by solid-phase combinatorial chemistry techniques. The present invention provides a method of synthesis of the compounds of the invention by a single-bead combinatorial strategy whereby the structure of each compound is known. The present method thus avoids the difficulties inherent in other prior art combinatorial syntheses, for example the need for sophisticated tagging schemes or extensive analytical techniques to identify the synthesized compounds.

The method of synthesizing the compounds of the present invention comprises coupling a diprotected glutamate moiety to a solid support, deprotecting the glutamate amino-terminus, adding the hydrophobic residue R'" COX, wherein X is a leaving group such as chloride, anhydride, active ester, pentafluorophenyl, phosphate derivative or phosphonate derivative, deprotecting the glutamate carboxy-terminus, adding protected diamine having the formula A-$NHCH_2CH_2NH(R")$ wherein A is a protection group, deprotecting the amino-terminus of the diamine, adding an oxazole carboxylic acid having the formula

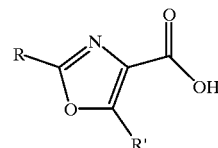

and cleaving the resulting compound from the solid support. By coupling protected glutamate to the solid support on a large scale, and distributing batches of the growing compound to different vessels at each step, for example after the removal of each protecting group, a large number of compounds can be synthesized during each reaction run by varying the R, R', R" and R'" groups. A representative synthetic scheme is set forth in FIG. 2.

Solid supports for combinatorial synthesis are known to those of ordinary skill in the art. In a preferred embodiment of the present invention, the solid support is a polystyrene resin. In a more preferred embodiment, the solid support is the polystyrene resin described by Wang (1973) *J. Amer. Chem. Soc.* 95: 1328, and also known as the Wang resin. The Wang resin is commercially available, for example from Advanced Chemtech. Other suitable solid supports include polyethylene glycol-polystyrene graft or Rink resins.

Diprotected glutamate may be prepared by methods known in the art. The skilled artisan is aware of suitable protecting groups for the amino- and carboxy-termini of glutamate, which are reviewed for example by Greene et al. *Protective groups in organic synthesis*, 2nd edition, Wiley, N.Y., 1991. In a preferred embodiment the amino-terminal protecting group is Fmoc and the carboxyl-terminal protecting group is a γ-allyl ester group. This preferred diprotected glutamate may be synthesized by protecting the carboxylic function with the allyl ester as described by Belshaw et al. (1990) *Syn Comm.* 20: 3157, followed by treatment with Fmoc-Cl. According to the method of Belshaw et al., chlorotrimethylsilane is added to a suspension of L-glutamic acid in dry allyl alcohol under $N_2$ and stirred for 18 hours, followed by the addition of ethyl ether.

Diprotected glutamate is coupled to a solid support by methods known to those of ordinary skill in the art and appropriate for the desired support. In a preferred embodiment, diprotected glutamate is coupled to the Wang resin with 1-ethyl-3-[3-(dimethylamino)propyl]-carbodiimide hydrochloride (EDCl) on a large scale to provide a supply of solid phase beads coupled to diprotected glutamate. Other suitable coupling methods are reviewed for example by Bodanszky, *Principles of peptide synthesis*, 2nd edition, Springer, Berlin, 1993, and include DCC, HOBt, BOC reagents, and others.

The glutamate amino-terminus is deprotected by a method appropriate to the protecting group. For example, a base labile group such as Fmoc may be removed by treatment with piperidine and tetrahydrofuran (THF). At this point the resin may be distributed to a number of separate vessels in order that compounds having different R'" substituents may be prepared. For example, the resin may be distributed to multiple filters equipped with inert gas inlets for maintaining steady bubbling and suction adapters. After the addition of solvent, hydrophobic residues R'" COX are added to each flask. Thus different amide derivatives are provided, the number of which is determined by the number of vessels to which the resin has been distributed and the number of different R'" substituents. By adding R'" COX having differing R'" groups to each vessel, the final compounds can be conveniently identified. R'" $CO_2H$ or R'" COX may be prepared by standard solution synthesis or obtained commercially.

Figure 3:
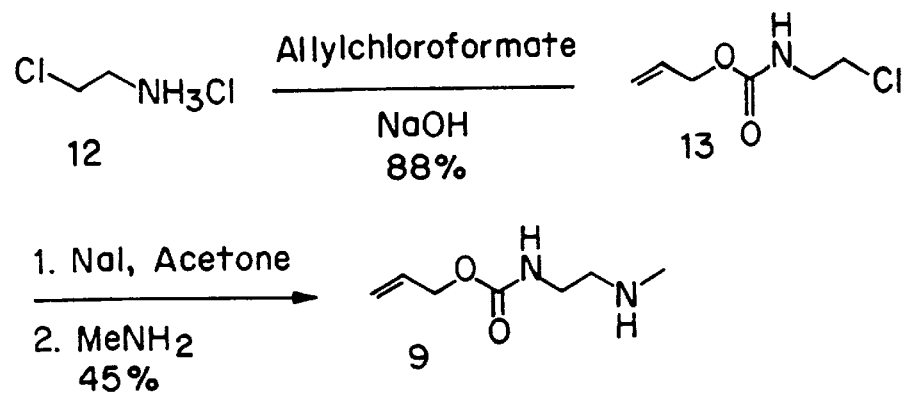
FIG. 3 presents a scheme for a general synthetic route to monoprotected ethylene diamines.

After filtration and rinsing of the solid support, the carboxy-terminal protecting group is removed by a method suitable for the protecting group. For example, allyl esters may be removed by Pd(O) chemistry as described by Dangles et al. (1987) *J. Org. Chem.* 52: 4984. The resin may again be divided into batches at this point and distributed into separate vessels such as the filters described above so that compounds containing different R" groups may be prepared. The protected diamine is then added with a suitable coupling agent so that the side chain carboxyl terminus of glutamate is extended. In a preferred embodiment the protecting group of the diamine is an N-allyloxycarbonyl group such that the diamine has the formula Alloc-NHCH$_2$CH$_2$NH(R"). Suitable coupling agents include for example PyBroP$^{60}$ and CloP$^{61}$. Alloc-NHCH$_2$CH$_2$NH(R") may be conveniently prepared by carbamoylation of chloroethylamine followed by treatment with sodium iodide and commercially available amine R"NH$_2$, as depicted in FIG. 3.

The resulting compounds are deprotected, at which point the compounds may be again distributed to different vessels for the addition of different R and R' substituents. Coupling with oxazole carboxylic acids having the formula

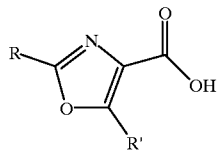

wherein R and R' are as defined above for formula I, in the presence of CloP, followed by rinsing with solvent provides the compounds of the invention attached to the solid support. The oxazole carboxylic acids may be prepared separately in solution phase from carboxylic acids having the structure R—CO$_2$H wherein R is as defined above for formula I and serine methyl ester, threonine methyl ester and phenyl serine methyl ester. An oxidation-cyclodehydration protocol depicted in FIG. 4 and described by Wipf et al. (1993) *J. Org. Chem.* 58: 3604, followed by saponification yields the desired carboxylic acid segments. The intermediate oxazole esters may be purified by column chromatography on SiO$_2$.

The carboxylate may be released from the support by complete or partial cleavage with 50% trifluoroacetic acid to provide the compounds of the invention. After filtration of the solid support and evaporation of the resulting mother liquor, the compounds of Formula I are chemically pure and structurally well-defined.

It has been found in accordance with the present invention that compounds of formula I are capable of inhibiting serine/threonine protein phosphatases. Inhibition of serine/threonine protein phosphatases is defined herein as inhibition of the activity of one or more of PP1, PP2A or PP3 at a concentration of 100 $\mu$M or less of the inhibitor compound. In a preferred embodiment, the activity of the phosphatase is inhibited by at least 10%. In more preferred embodiments, the activity of the phophatase is inhibited by at least 25%, or even more preferably, by at least 50%. Inhibition of PP1, PP2A or PP3 can be assessed by methods known to one of ordinary skill in the art. Suitable assays are described, for example by Honkanen et al.(1994) *Toxicon* 32:339 and Honkanen et al. (1990) *J. Biol. Chem.* 265: 19401, the disclosures of which are incorporated herein by reference. Briefly, phosphatase activity is determined by quantifying the [$^{32}$P] released from a $^{32}$P-labeled substrate such as phosphohistone or phosphorylase-a. Decreased [$^{32}$P] release in the presence of the compounds of the present invention relative to control samples provides a measure of the ability of the compounds of the invention to inhibit PP1, PP2A or PP3.

In another suitable assay, the ability of the compounds of the present invention to inhibit the activity of protein phosphatase PP2A is assessed. The activity of the catalytic subunit of bovine cardiac muscle PP2A (Gibco-BRL, Gaithersburg, Md.) is measured in 96-well microtiter plates using the substrate fluorescein diphosphate as follows. Inhibitors are resuspended in DMSO, which is also used as the vehicle control. An incubation mixture of 150 $\mu$L is prepared containing 25 mM Tris, pH 8.0, 5 mM EDTA, 33 $\mu$g/ML BSA, 20 $\mu$M fluorescein diphosphate, and 100 $\mu$M inhibitor or DMSO control. Reactions are initiated by adding 0.2 units of PP2A, and incubated at room temperature overnight. Fluorescence emission from the product is measured spectrofluorometrically, for example with Perseptive Biosystems Cytofluor II (Framingham, Mass.) (excitation filter, 485 nm; emission filter, 530 nm). The rate of increase in absorbance due to formation of dephosphorylated substrate is proportional to phosphatase activity. Thus, decreased absorbance relative to control samples provides a measure of the ability of the present compounds to inhibit the phosphatase.

The compounds of the present invention are also capable of inhibiting dual specificity phosphatases, for example CDC25A and CDC25B. Phosphatases CDC25A and CDC25B are disclosed in U.S. Pat. No. 5,441,880. Inhibition of dual specificity phosphatases is defined herein as inhibition of the activity of CDC25A and/or CDC25B at a concentration of 100 $\mu$M of the inhibitor compound. In a preferred embodiment, the activity of the phosphatase is inhibited by at least 10%. In more preferred embodiments, the activity of the phophatase is inhibited by at least 25%, or even more preferably, by at least 50%. The ability of the compounds of the present invention to inhibit the phosphatases can be determined by measuring the effect of the compounds on the ability of CDC25 or CDC25B to dephosphorylate a substrate. Appropriate methods are known to those of ordinary skill in the art, and include, for example, calorimetric assays. A suitable assay is described in U.S. Pat. No. 5,441,880, the disclosure of which is incorporated herein by reference. As disclosed therein, the compound to be tested is combined with CDC25A or CDC25B and an appropriate CDC25 substrate, such as p-nitrophenyl phosphate or inactive cyclin/cdc2, and the ability of the compound to inhibit the phosphatase activity of CDC25 is assessed. Phosphatase activity may be assessed by known techniques, such as measuring optical density and comparing it to the optical density of a control sample that does not contain the inhibitor. The assay may be performed as a rapid calorimetric microtitration plate assay.

The compounds of the present invention are useful as inhibitors of protein phosphatases. It is known that inhibition of protein phosphatases results in increased protein phosphorylation in vitro and in cells. Sassa et al. (1989) *Biochem. Biophys. Res. Comm.* 159: 939; Yatsunami et al.(1991) *Biochem. Biophys. Res. Commun.* 177: 1165. Thus the compounds are useful to inhibit protein dephosphorylation, for example in in vitro assays in which phosphorylated proteins are measured or detected, or in methods in which proteins are labeled by phosphorylation. For example, proteins are commonly labeled with $^{32}$P to facilitate detection. Inclusion of a compound of the present invention is useful to prevent dephosphorylation by endogenous phosphatases. Further, phosphatases are known to have multiple functions, including but not limited to regulation of signal transduction, cell adhesion, gene transcription, RNA splicing, apoptosis, mitosis and cell proliferation. Thus inhibitors of protein phosphatases are useful in the alteration of various cellular functions. In particular, the present compounds are useful as inducers of apoptosis and inhibitors of cell proliferation.

Accordingly, the present invention provides a method of inhibiting a protein phosphatase comprising contacting a phosphatase-inhibiting effective amount of a compound having the formula:

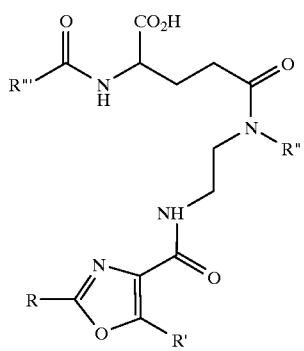

I with a protein phosphatase under conditions whereby the activity of the protein phosphatase is inhibited. In a preferred embodiment, R, R', R" and R''' are independently H, alkyl, alkenyl, alkynyl, cycloalkyl, phenyl (Ph), oxetanyl, azetidinyl, furanyl, pyrrole, indolyl, oxazolyl, isoxazolyl, imidazolyl, pyrazolyl, triazolyl, tetrazolyl, pyranyl, pyridyl, pyridonyl, piperidyl, piperazinyl, quinolyl, azepinyl, and diazepinyl. In another preferred embodiment, R and R''' are independently Ph, $CH_3$, n-$C_5H_{11}$, n-$C_7$ $H_{15}$, n-$C_9H_{19}$, PhCHCH, $PhCH_2CH_2$, $Ph(CH_2)_2CC(CH_3)$, (p-MeO)Ph, (p-MeNHCO)Ph, $PhCHC(CH_3)CH_2CH_2$, $Ph(CH_2)_2CHCHCHCH$, $Ph(CH_2)_3CHC(CH_3)CHCH$, $C_6H_{13}CH(CH_3)CHC(CH_3)CHCH$, or $C_4H_9CH(CH_3)CHC(CH_3)CHC(CH_3)$, R' is H, $CH_3$ or Ph, and R" is H, $CH_3$, benzyl (Bn), $CH_2CH(CH_3)$, n-$C_6H_{13}$, $CH_2CH_2NBn$, $CH_2CH_2Ph$, or $(CH_2)_3Ph$. In a most preferred embodiment, R is Ph, R' is Ph, R" is Bn or $CH_3$ and R''' is n-$C_9H_{19}$. In a preferred embodiment the protein phosphatase is a serine/threonine phosphatase. In a more preferred embodiment the protein phosphatase is PP1, PP2A or PP3. In another preferred embodiment the phosphatase is a dual specificity phosphatase, including, for example, CDC25A and CDC25B. The skilled artisan readily can determine the amount of the phosphatase inhibitor that is required to inhibit protein phosphatase by measuring phosphatase activity in the presence and absence of the inhibitor. Phosphatase activity can be determined by assessing the dephosphorylation of a substrate as described hereinabove, or by measuring parameters that are known to result from phosphatase activity. For example, phosphatase inhibition by the compounds of the present invention can be assessed by measuring inhibition of cell proliferation in response to treatment of cells with the present compounds.

The compounds of the present invention are also useful as antiproliferative agents. The CDC25 enzymes are positive regulators of cell cycle progression. For example, CDC25C drives entry into mitosis by dephosphorylating and thereby activating the mitotic inducer cdc2. U.S. Pat. No. 5,294,538 discloses that dephosphorylation of cdc2 by the CDC25 phosphatase activates the M phase-promoting factor (MPF) that triggers the G2/M transition of the cell cycle, and that inhibition of the CDC25 phosphatase activity inhibits entry of cells into mitosis. Further, CDC25A and CDC25B act as oncogenes, and CDC25B is over-expressed in one third of primary human breast cancers (Galaktionov et al., (1995) Science 269: 1575) and is elevated in other human tumor cell types and in virally transformed cells (Nagata et al.(1991) New Biologist 3:959). It is also known that cell proliferation is coordinated by cyclin-dependent kinases, and tightly controlled by both kinases and phosphatases. The cell cycle regulating activity of CDC25 is controlled by PP2A. Hunter et al.(1994) Cell 79: 573. Thus, inhibition of PP1 or PP2A may also result in disrupted cell cycle transition. It has been demonstrated in accordance with the present invention that compounds of the invention inhibit proliferation of cells by reducing the number of cells in inhibitor-treated versus untreated cell cultures. Accordingly, the present invention further provides a method of inhibiting cell proliferation comprising introducing into cells a proliferation-inhibiting amount of a compound of formula I. In a preferred embodiment the compound has formula I wherein R is Ph, R' is Ph, R" is Bn and R''' is n-$C_9H_{19}$. In another preferred embodiment the cells are tumor cells. In still another preferred embodiment the cells are human breast cancer cells.

The ability of the compounds of the present invention to inhibit proliferation can be assessed by methods known to those of ordinary skill in the art. For example, proliferating cells can be contacted with a compound of the invention, and cell numbers determined. A reduction in cell number in treated versus untreated cells provides a measure of the ability of the present compounds to inhibit proliferation. In a preferred embodiment the cells to be treated are cancer cells, for example breast cancer cells such as the CDC25B+ breast cancer cells MDA-MB-231, which are available from the American Type Culture Collection (Accession No. HTB-26). The antiproliferative activity of the present compounds can also be measured by the assay described by Lazo et al.(1995) J. Biol. Chem. 270: 5506, the disclosure of which is incorporated herein by reference. The microtiter-based calorimetric assay is based upon the reduction of 3-[4,5-dimethylthiazol-2-yl]-2,5-diphenyl tetrazolium bromide by living cells, and permits evaluation of the cytostatic or cytotoxic actions of large numbers of compounds quickly in mouse embryonic fibroblasts and human CDC25B+ breast cancer cells. Briefly, exponentially growing CDC25B+ MDA-MB-231 cells are treated continuously with from 0 to 100 $\mu$M of a compound of the invention, and cell proliferation is determined calorimetrically after 72 hours by assessing the ability of the cells to reduce 3-[4,5-dimethylthiazol-2-yl]-2,5-diphenyl tetrazolium bromide.

The antiproliferative ability of the compounds of the present invention can also be measured in an in vivo tumor reduction assay. Athymic (nu/nu) and severe combined immunodeficiency (SCID) mice provide well-recognized models for antitumor activity. Mice are injected subcutaneously (s.c.) with $10^6$ MDA-MB-231 cells in 100 $\mu$l phosphate buffered saline (PBS). Once tumors reach a palpable size (100 $mm^2$), mice are treated once daily orally (p.o.), intraperitoneally (i.p.) or subcutaneously (s.c.) with 0, 0.1, 1, 10 or 30 mg/kg of a compound of the present invention for five days. Tumor mass is measured with a vernier caliper and calculated as described by Jani et al. (1992) Cancer Res. 52: 2931. Reduction in tumor mass in treated versus untreated mice is indicative of antiproliferative activity of the compounds of the invention. Pharmacological principles may be used to optimize the dose and schedule of administration and are readily within the skill of those in the art.

The present invention also provides pharmaceutical compositions comprising a compound of the present invention and a pharmaceutically acceptable carrier or diluent. As used herein, the term "pharmaceutically acceptable carrier or diluent" means any and all solvents, dispersion media, antibacterial and antifungal agents, microcapsules, liposomes, cationic lipid carriers, isotonic and absorption delaying agents and the like which are not incompatible with the active ingredients. The use of such media and agents for pharmaceutically active substances is well known in the art. Supplementary active ingredients may also be incorporated into the compositions and used in the methods of the invention.

The formulation of pharmaceutical compositions is generally known in the art and reference can conveniently be made to Remington's Pharmaceutical Sciences, 17th ed., Mack Publishing Co., Easton, Pa. Formulation of the compounds of the present invention must be stable under the conditions of manufacture and storage and also must be preserved against the contaminating action of microorganisms such as bacteria and fungi. Prevention against microorganism contamination can be achieved through the addition of various antibacterial and antifungal agents.

The pharmaceutical forms of the compounds of the invention suitable for administration include sterile aqueous solutions or dispersions and sterile powders for the extemporaneous preparation of sterile injectable solutions or dispersions. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, and vegetable oils. Isotonic agents such as sugars or sodium chloride may be incorporated into the subject compositions.

The compounds of the invention are compounded for convenient and effective administration in effective amounts with a suitable pharmaceutically acceptable carrier, preferably in dosage unit form. Dosage unit form as used herein refers to physically discrete units suited as unitary dosages for a subject to be treated, each unit containing a predetermined quantity of a compound of the invention calculated to produce the desired therapeutic effect in association with the required pharmaceutical carrier. The compositions may be administered in a manner compatible with the dosage formulation, in such amount as will be therapeutically effective, and in any way which is medically acceptable. Possible administration routes include oral route and parenteral administration such as intravascular, intravenous, intraarterial, subcutaneous, intramuscular, intratumor, intraperitoneal, intraventricular and intraepidural. The compositions may also be directly applied to tissue surfaces. Sustained release administration, for example by depot injections or erodible implants, is also specifically included.

The invention is further illustrated by the following specific examples which are not intended in any way to limit the scope of the invention.

EXAMPLE I

Figure 5:
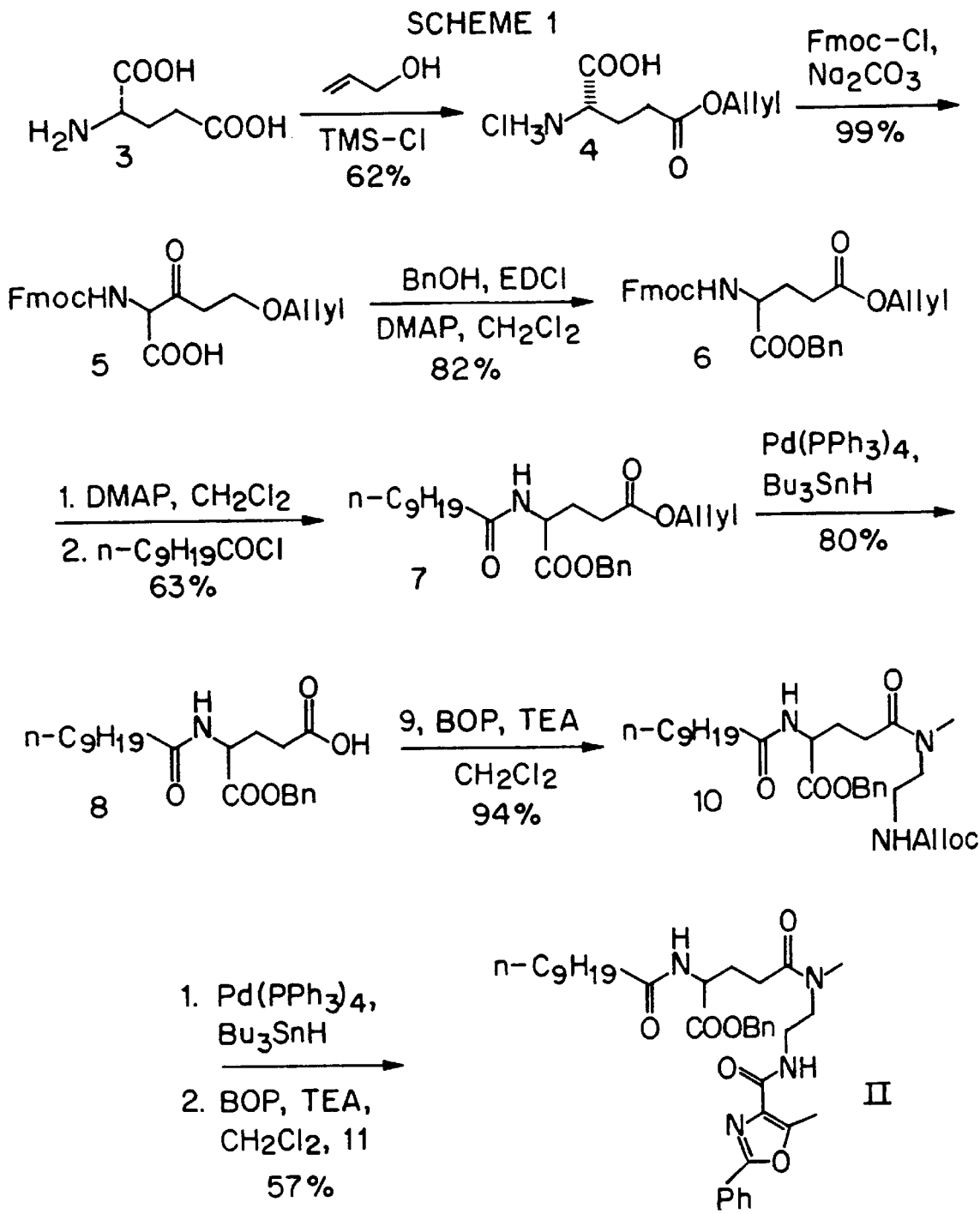
FIG. 5 shows a scheme for the solution phase synthesis of model compound II.

A method for the combinatorial synthesis of compounds of formula I (FIG. 2) was developed by optimizing a solution phase synthesis of model compound II. The solution phase synthesis of model compound II is depicted in FIG. 5 and proceeded as follows:

All glassware was dried in an oven at 150° C. prior to use. THF and dioxane were dried by distillation over Na/benzophenone under a nitrogen atmosphere. Dry $CH_2Cl_2$, DMF and $CH_3CN$ were obtained by distillation from $CaH_2$.

L-Glutamic acid (3) was protected in 62% yield as the γ-allyl ester using allyl alcohol and chlorotrimethylsilane to provide 2-amino-pentanedioic acid 5-allyl ester 4 as follows:

To a stirred suspension of 2.5 g (16.9 mmol) of L-glutamic acid (3) in 40 mL of dry allyl alcohol was added dropwise 5.4 mL (42.3 mmol) of chlorotrimethylsilane. The suspension was stirred at 22° C. for 18 h and poured into 300 mL of $Et_2O$. The resulting white solid was filtered off, washed with $Et_2O$, and dried in vacuo to provide 3.80 g (62%) of ester 4: Mp 133–134.5° C. ($Et_2O$); IR (KBr) 3152, 2972, 2557, 1738, 1607, 1489, 1450, 1289, 1366, 1264, 1223, 1177, 1146, 121, 1084 $cm^{-1}$; $^1H$ NMR ($D_2O$) δ 5.8–5.7 (m, 1 H), 5.14 (dd, 1 H, J=1.4, 17.3 Hz), 5.09 (dd, 1 H, J=1.0, 10.4 Hz), 4.44 (d, 2 H, J=5.6 Hz), 3.92 (t, 1 H, J=6.8 Hz), 2.48 (t, 2 H, J=7.0 Hz), 2.1–2.0 (m, 2 H); $^{13}C$ NMR (DMSO-$d_6$) δ 171.5, 170.6, 132.7, 117.9, 64.7, 51.2, 29.3, 25.2; MS (EI) m/z (relative intensity) 188 (63), 142 (72), 128 (27), 100 (21), 85 (100), 74 (32), 56 (73).

Treatment with Fmoc as follows provided 2-(9-H-Fluoren-9-ylmethoxycarbonylamino)-pentanedioic acid 5-allyl ester 5. To 20 mL of dioxane was added 1.5 g (6.7 mmol) of ester 4. The resulting suspension was treated with 16.8 mmol (17.7 mL of a 10% solution) of sodium carbonate at 0° C., stirred for 5 min and treated with 1.74 g (6.7 mmol) of Fmoc-Cl dissolved in 10 mL of dioxane. The reaction mixture was warmed to 22° C., stirred for 3 h, poured into 50 mL of $H_2O$ and extracted with $Et_2O$ (2×25 mL). The aqueous layer was cooled to 0° C., acidified to pH 1 with concentrated HCl, and extracted with EtOAc (3×25 mL). The resulting organic layer was dried ($Na_2SO_4$) and concentrated in vacuo to give 2.72 g (99%) of 5 as a viscous oil: $[\alpha]_D$+8.5° (c 2.8, $CHCl_3$, 21° C.); IR (neat) 3312, 3061, 2951, 2361, 2349, 2332, 1725, 1528, 1447, 1414, 1325, 1254, 1117, 1078, 1049 $cm^{-1}$; $^1H$ NMR δ 11.09 (bs, 1 H), 7.73 (d, 2 H, J=7.5 Hz), 7.57 (d, 2 H, J=5.1 Hz), 7.4–7.25 (m, 4 H), 6.0–5.85 (m, 1 H), 5.76 (d, 1 H, J=8.1 Hz), 5.30 (d, 1 H, J=19.5 Hz), 5.21 (d, 1 H, J=10.5 Hz), 4.6–4.35 (m, 5 H), 4.19 (t, 1 H, J=6.6 Hz), 2.5–2.2 (m, 4 H); $^{13}C$ NMR δ 175.6, 172.6, 156.2, 143.7, 143.5, 141.2, 131.7, 127.6, 127.0, 125.0, 119.9, 118.4, 67.1, 65.4, 53.1, 46.9, 30.2, 27.1; MS (EI) m/e (relative intensity) 409 (7), 351 (19), 338 (12), 280 (11), 239 (11), 196 (12), 178 (100), 165 (40); HRMS (EI) calculated for $C_{23}H_{23}NO_6$: 409.1525, found: 409.1501.

Treatment with Fmoc-Cl followed by coupling to benzyl alcohol using 1-ethyl-3-[3-(dimethylamino)propyl]-carbodiimide [by] hydrochloride (EDCL) provided 2-(9H-Fluoren-9-ylmethoxycarbonylamino)-pentanedioic acid 5-allyl ester 1-benzyl ester 6 in 82% yield. To a solution of 1.5 g (36.6 mmol) of 5 in 5 mL of $CH_2Cl_2$ was added 0.42 mL (40.3 mmol) of benzyl alcohol, 0.912 g (47.6 mmol) of EDCI, and 45 mg (3.66 mmol) of dimethylaminopyridine (DMAP). The reaction mixture was stirred at 22° C. for 6 h, diluted with 20 mL of $CH_2Cl_2$, and extracted with $H_2O$ (1×15 mL), 0.1M HCl (2×15 mL), and brine (2×10 mL). The organic layer was dried ($Na_2SO_4$), concentrated in vacuo, and chromatographed on $SiO_2$ (Hexanes/EtOAc, 5:1) to give 1.83 g (82%) of 6 as a white solid: Mp 66.2–67.1° C. (EtOAc/Hexanes); $[\alpha]_D$ +1.40° (c 1.64, $CHCl_3$, 21° C.); IR (neat) 3314, 1726, 1682, 1527, 1443, 1414, 1383, 1254, 1173, 1099, 1082, 980, 754, 735 $cm^{-1}$; $^1H$ NMR δ 7.75 (d, 2 H, J=7.4 Hz), 7.59 (d, 2 H, J=7.1 Hz), 7.41–7.27 (m, 9 H), 5.95–5.85 (m, 1 H), 5.44 (d, 1 H, J=8.2 Hz), 5.34–5.19 (m, 4 H), 4.56 (d, 2 H, J=5.6 Hz), 4.5–4.4 (m, 3 H), 4.21 (t, 1 H, J=7.0 Hz), 2.5–2.0 (m, 4 H); $^{13}C$ NMR δ 172.2, 171.6, 155.8, 143.7, 143.5, 141.1, 135.0, 131.8, 128.5, 128.3, 128.1, 127.6, 126.9, 124.9, 119.8, 118.3, 67.2, 66.9, 66.2, 53.3, 47.0, 28.0, 27.3; MS (FAB, MNBA/MeOH) m/z (relative intensity) 500 ([M+H]+, 40), 465 (8), 448 (14), 433 (12), 413 (8), 386 (38), 371 (24), 349 (9), 324 (16), 309 (26), 293 (11), 265 (10), 247 (24), 231 (56), 215 (39), 202 (26), 191 (24), 179 (67), 165 (48), 154 (67), 143 (31), 133 (71), 117 (100).

The Fmoc protective group was subsequently removed by exposure to DMAP and the free amine was acylated in situ with decanoyl chloride to give 2-Decanoylamino-pentanedioic acid 5-allyl ester 1-benzyl ester (7) in 63% yield as follows. To a suspension of 1 g (2.0 mmol) of 6 in 10 mL of $CH_2Cl_2$ was added 1 g (8.2 mmol) of DMAP. The reaction mixture was stirred at 22° C. for 24 h, treated with 0.62 mL (3.0 mmol) of decanoyl chloride, stirred for 2 h at 22° C., and extracted with saturated sodium bicarbonate solution (2×10 mL). The organic layer was dried ($Na_2SO_4$), evaporated to dryness, and the residue was chromatographed on $SiO_2$ (Hexanes/EtOAc, 5:1) to give 548 mg (63%) of 7 as a viscous oil: IR (neat) 3293, 3063, 2924, 2855, 1740, 1649, 1534, 1453, 1379, 1175, 986, 930 cm$^{-1}$; $^1$H NMR δ 7.26 (s, 5 H), 6.68 (d, I H, J=7.8 Hz), 5.85–5.75 (m, 1 H), 5.22 (d, 1 H, J=17.3 Hz), 5.14 (d, 1 H, J=10.4 Hz), 5.08 (s, 2 H), 4.63–4.57 (m, 1 H), 4.48 (d, 2 H, J=5.6 Hz), 2.38–2.28 (m, 2 H), 2.2–2.1 (m, 3 H), 2.0–1.9 (m, 1 H), 1.55 (t, 2 H, J=6.9 Hz), 1.20 (bs, 12 H), 0.82 (t, 3 H, J=5.9 Hz); $^{13}$C NMR δ 173.0, 172.1, 171.6, 135.0, 131.7, 128.2, 128.1, 127.8, 117.9, 66.8, 64.9, 51.3, 36.0, 31.6, 29.9, 29.1, 29.0, 26.8, 25.3, 22.3, 13.8; MS (El) m/z (relative intensity) 431 (12), 319 (21), 296 (51), 142 (100), 124 (31), 91 (91); HRMS (El) m/z calculated for $C_{25}H_{37}NO_5$: 431.2672, found: 431.2673.

Pd(O)-catalyzed deprotection of the allyl ester proceeded as follows to yield 2-Decanoylamino-pentanedioic acid 1-benzyl ester (8). To a solution of 752 mg (1.74 mmol) of 2-decanoylamino-pentanedioic acid 7 in 10 mL of $CH_2Cl_2$ was added 100 mg (0.087 mmol) of tetrakistriphenylphosphine Pd(O) followed by 0.52 mL (1.9 mmol) of tributyltin hydride. After 15 min, the reaction mixture was quenched with 10 mL of a 10% HCl solution. The aqueous layer was reextracted with 15 mL of $CH_2Cl_2$ and the organic layer dried ($Na_2SO_4$), concentrated in vacuo, and chromatographed on $SiO_2$ (Hexanes/EtOAc, 9:1) to provide 545 mg (79.9%) of 8 as a thick oil: $[\alpha]_D$ +2.8° (c 1.2, $CHCl_3$, 21° C.); IR (neat) 3351, 3064, 2995, 2852, 1738, 1712, 1657, 1536, 1454, 1380, 1364, 1265, 1209, 1183, 1121, 739 cm$^{-1}$; $^1$H NMR δ 10.9–10.7 (bs, 1 H), 7.22 (s, 5 H), 6.58 (d, 1 H, J=7.8 Hz), 5.09 (s, 2 H), 4.63 (dd, 1 H, J=8.1, 12.9 Hz), 2.4–2.25 (m, 2 H), 2.2–2.1 (m, 3 H), 2.0–1.9 (m, 1 H), (m, 6 H), 1.53 (t, 2 H, J=6.6 Hz), 1.19 (bs, 12 H), 0.81 (t. 3 H, J=6.0 Hz); $^{13}$C NMR δ 176.9, 174.0, 171.8, 134.9, 128.5, 128.4, 128.1, 67.3, 51.4, 36.2, 31.7, 29.9, 29.3, 29.2, 29.1, 27.0, 25.5, 22.5, 14.0; MS (El) m/z (relative intensity) 391 (54), 373 (62), 279 (13), 256 (19), 178 (27), 178 (23), 155 (13), 146 (6), 130 (7), 102 (100); HRMS (El) m/z calculated for $C_{22}H_{33}NO_5$:391.2358, found: 391.2350.

Coupling to ethylene diamine (9) yielded 4-[(2-Allyloxycarbonylamino-ethyl)-methyl-carbamoyl]-2-decanoylamino-butyric acid benzyl ester (10). To a solution of 526 mg (1.3 mmol) of 8 in 10 mL of $CH_2Cl_2$ was added 225 μL (1.61 mmol) of triethylamine and 320 mg (2.0 mmol) of secondary amine 9. The solution was stirred at 22° C. for 5 min, treated with 710 mg (1.61 mmol) of benzotriazol-1-yloxytris (dimethylamino)phosphonium hexafluorophosphate (BOP reagent), stirred at 22° C. for 10 min, concentrated in vacuo, dissolved in 15 mL of EtOAc, and extracted with 2M HCl solution. The organic layer was chromatographed on $SiO_2$ (Hexanes/EtOAC, 1:3) to give 715 mg (94%) of 10 as a clear oil: $[\alpha]_D$ +5.3 (c 0.58, $CHCl_3$, 21° C.); IR (neat) 3420, 3250, 2924, 1713, 1680, 1657, 1642, 1632, 1537, 1495, 1470, 1455, 1252, 845 cm$^{-1}$; $^1$H NMR δ 7.35–7.2 (bs, 5 H), 6.97 (d, 0.3 H, J=7.5 Hz), 6.82 (d, 0.7 H, J=7.3 Hz), 5.9–5.6 (m, 2 H), 5.3–5.1 (m, 4 H), 4.65–4.5 (m, 1 H), 4.50 (d, 2 H, J=4.9 Hz); 3.55 (t, 1 H, J=7.0 Hz), 3.35–3.1 (m, 3 H), 2.85 (s, 3 H), 2.4–1.8 (m, 6 H), 1.65–1.5 (m, 2 H), 1.22 (bs, 12 H), 0.84 (t, 3 H, J=6.1 Hz); $^{13}$C NMR (MEOD) δ 176.4, 176.3, 174.4, 174.2, 173.2, 158.6, 137.1, 134.3, 134.2, 132.9, 129.5, 129.2, 129.1, 117.6, 117.4, 67.8, 66.3, 66.2, 53.5, 53.3, 39.6, 39.3, 36.7, 36.6, 34.2, 32.9, 30.5, 30.4, 30.3, 30.2, 29.7, 27.6, 26.8, 23.6, 14.5; MS (El) m/z (relative intensity) 531 (16), 473 (37), 418 (16), 396 (26), 374 (38), 361 (17), 338 (87), 220 (54), 184 (52), 155 (36), 130 (29), 101 (37), 91 (100); HRMS (El) m/z calculated for $C_{29}H_{45}N_3O_6$:531.3308, found: 531.3316.

Monoprotected ethylene diamines 9 were easily achieved by carbamoylation of 2-chloroethylamine monohydrochloride (12), Finkelstein reaction, and aminolysis (FIG. 3).

(2-Chloro-ethyl)-carbamic acid allyl ester (13) was synthesized as follows. A solution of 2.5 g (22 mmol) of chloroethylamine hydrochloride in 10 mL of 6M NaOH was cooled to 0° C. and treated dropwise with 2.7 mL (25.9 mmol) of allyl chloroformate while keeping the pH at 9 by addition of 6M NaOH solution. The reaction was then warmed to 22° C., stirred for 2 h, and extracted with THF. The organic layer was dried ($Na_2SO_4$, concentrated in vacuo, and chromatographed on $SiO_2$ (Hexanes/EtOAc, 9:1) to give 3.1 g (88%) of 13 as a yellow oil: IR (neat) 3333, 2949, 2348, 1705, 1647, 1529, 1433, 1368, 1248, 1190, 1144, 1061, 991, 929, 776 cm$^{-1}$; $^1$H NMR δ 6.05–5.85 (m, 1 H), 5.55–5.35 (bs, 1 H), 5.26 (dd, 1 H, J=1.5, 17.1 Hz), 5.18 (dd, 1 H, J=1.0, 10.4), 4.54 (d, 2 H, J=5.5 Hz), 3.57 (t, 2 H, J=5.5 Hz), 3.5–3.35 (m, 2 H); $^{13}$C NMR δ 156.0, 132.5, 117.7, 65.6, 43.8, 42.7.

To produce (2-Methylamino-ethyl)-carbamic acid allyl ester (9), a solution of 14 g (86 mmol) of 13 and 25 g (172 mmol) of sodium iodide in 40 mL of acetone was refluxed for 18 h, concentrated in vacuo, dissolved in $H_2O$, and extracted with $CH_2Cl_2$. The organic layer was dried ($Na_2SO_4$) and cooled to 0° C. Methyl amine was bubbled through the reaction mixture until the solution was saturated. The reaction mixture was warmed to 22° C., stirred for 36 h, concentrated in vacuo and chromatographed on $SiO_2$ (EtOAc) to produce 6.14 g (45%) of 9 as a yellow oil: IR (neat) 3306, 2938, 2313, 1844, 1703, 1651, 1525, 1460, 1383, 1256, 1144, 995, 927, 775 cm$^{-1}$; $^1$H NMR δ 5.95–5.8 (m, 1 H), 5.28 (dd, 1 H, J=1.4, 17.3 Hz), 5.18 (d, 1 H, J=10.4 Hz), 4.54 (d, 2 H, J=5.3 Hz), 4.9–4.6 (bs, 1 H), 3.34 (q, 2 H, J=5.6 Hz), 2.79 (t, 2 H, J=5.6 Hz), 2.47 (s, 3 H); $^{13}$C NMR δ 157.22, 132.8, 117.6, 65.5, 50.7, 39.7, 35.4; MS (El) m/e (relative intensity) 158 (32), 138 (17), 129 (25), 101 (13), 84 (12), 73 (13), 57 (100).

Figure 4:
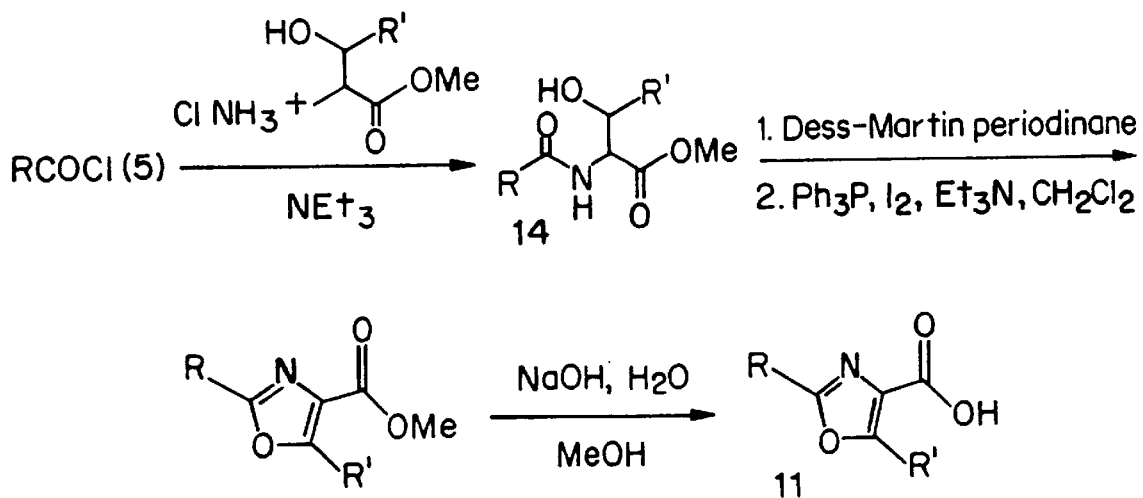
FIG. 4 shows a scheme for the synthesis of a heterocyclic moiety from N-benzoyl threonine.

The heterocyclic moiety 11 was prepared from N-benzoyl threonine (14) as follows and as depicted in FIG. 4.

5-Methyl-2-phenyl-oxazole-4-carboxylic acid methyl ester (15) was synthesized by treating a solution of 750 mg (3.2 mmol) of 14 in 10 mL of $CH_2Cl_2$ with 1.61 g (3.8 mmol) of Dess-Martin reagent. The reaction was stirred at 22° C. for 10 min, concentrated in vacuo, and chromatographed on $SiO_2$ (Hexanes/EtOAc, 3:2) to give 658 mg (89%) of 2-benzoylamino-3-oxo-butyric acid methyl ester. Alternatively, a solution of 9.12 g (38 mmol) of 14 in 80 mL of $CH_2Cl_2$ was cooled to −23° C. and treated with 16.1 mL (115-mmol) of triethylamine and a solution of 18.3 g (115 mmol) of $SO_3$-pyridine complex in 60 mL of dry DMSO. The reaction mixture was warmed to 22° C., stirred for 30 min, then cooled to −48° C. and quenched with 20 mL of saturated NaHCO$_3$. The solution was extracted with 50 mL of Hexanes/EtOAc, 2:1. The aqueous layer was reextracted with Hexanes/Et$_2$O, 2:1, and the combined organic layers were washed with brine, dried (Na$_2$SO$_4$), and chromatographed (Hexanes/EtOAc, 3:2) to give 7.1 g (79%) of 2-benzoylamino-3-oxo-butyric acid methyl ester as a white solid: Mp 112.7–113.3° C. (Hexanes/EtOAc); IR (neat) 3402, 1734, 1662, 1599, 1578, 1510, 1478, 1435, 1354, 1269, 1156, 1121, 912, 804, 714 cm$^{-1}$; $^1$H NMR 8.2–8.1 (bs, 1 H), 8.0–7.4 (m, 5 H), 5.49 (s, 1 H), 3.86 (s, 3 H), 2.33 (s, 3 H); $^{13}$C NMR δ 168.2, 167.2, 132.6, 132.5, 132.1, 128.7, 127.3, 83.9, 54.2, 23.2; MS (El) m/e (relative intensity) 235 (13), 208 (18), 192 (8), 121 (7), 105 (100), 77 (58).

A solution of 277 mg (1.06 mmol) of triphenylphosphine, 268 mg (1.06 mmol) of iodine, and 0.29 mL (2.11 mmol) of triethylamine in 5 mL of CH$_2$Cl$_2$ was cooled to −48° C. and treated with a solution of 124 mg (0.528 mmol) of 2-benzoylamino-3-oxo-butyric acid methyl ester in 5 mL of CH$_2$Cl$_2$. The reaction mixture was warmed to 22° C., stirred for 20 min, transferred to a separatory funnel and extracted with aqueous sodium thiosuffate followed by saturated sodium bicarbonate. The organic layer was concentrated in vacuo and chromatographed on SiO$_2$ (Hexanes/EtOAc, 9:1) to give 84.4 mg (74%) of 15 as a white solid: Mp 89.3–89.9° C. (Hexanes/EtOAc); IR (neat) 3025, 1717, 1610, 1561, 1485, 1436, 1348, 1323, 1302, 1285, 1235, 1188, 1103, 1072, 1057, 1022 cm$^{-1}$; $^1$H NMR 8.1–7.95 (m, 2 H), 7.5–7.3 (m, 3 H), 3.92 (s, 3 H), 2.68 (s, 3 H); $^{13}$C NMR δ 162.7, 159.5, 156.3, 130.8, 128.8, 128.6, 128.3, 126.4, 51.9, 11.98; MS (El) m/z (relative intensity) 231 (6), 217 (51), 185 (55), 105 (100), 77 (4 1), 44 (64); HRMS (El) m/z calculated for C$_{12}$H$_{11}$NO$_3$:217.0739, found: 217.0729.

5-Methyl-2-phenyl-oxazole-4-carboxylic acid 11 we produced by stirring a solution of 2.07 g (9.5 mmol) of 15 in 20 mL of 3M NaOH and 12 mL of MeOH at 22° C. for 2 h and extracting with Et$_2$O. The aqueous layer was acidified to pH 1 with concentrated HCl and extracted with EtOAc. The organic layer was dried (Na$_2$SO$_4$), and concentrated in vacuo to give 1.84 g (95%) of 11 as an off-white solid: Mp 182.3–182.6° C. (EtOAc/Hexanes); IR (neat) 3200, 2950, 2932, 2890, 2363, 2336, 1694, 1682, 1611, 1563, 1483, 1450, 1337, 1255, 1192, 1117, 1053, 1020 cm$^{-1}$; $^1$H NMR δ 10.2–9.9 (bs, 1 H), 8.2–7.9 (m, 2 H), 7.6–7.4 (m, 3 H), 2.75 (s, 3 H); $^{13}$C NMR (CD$_3$OD) δ 164.6, 160.7, 157.4, 131.9, 129.8, 129.6, 127.3, 127.2, 12.1; MS (El) m/z (relative intensity) 203 (53), 185 (24), 157 (13), 116 (17), 105 (100), 89 (21), 77 (33), 63(16); HRMS calculated for C$_{11}$H$_9$NO$_3$: 203.0582, found: 203.0583.

2-Decanoylamino-4-(methyl-{3-[5-methyl-2-phenyloxazole-4-carbonyl]-ethyl}-carbamoyl)-butyric acid benzyl ester (formula II) was then provided as follows: To a solution of 193 mg (0.363 mmol) of 10 in 15 mL of CH$_2$Cl$_2$ was added 20 mg (0.018 mmol) of tetrakistriphenylphosphine Pd(0), 127 μL (0.472 mmol) of tributyltin hydride, and 20 μL of H$_2$O. The reaction mixture was stirred at 22° C. for 5 min, filtered through a plug of basic Al$_2$O$_3$ and treated with 150 mg (0.726 mmol) of oxazole 11, 60 μL (0.436 mmol) of triethylamine, and 192 mg (0.436 mmol) of BOP reagent. The reaction mixture was stirred for 30 min at 22° C., diluted with 10 mL of CH$_2$Cl$_2$, and extracted with saturated NaHCO$_3$ solution, 1M HCl, and brine. The organic layer was concentrated in vacuo and chromatographed on SiO$_2$ (Hexanes/EtOAc, 1:1) to give 131 mg (57%) of 2 as a viscous oil: [α]$_D$ −0.8° (c 1.32, CHCl$_3$, 21° C.); IR (neat) 3476, 3415, 3311, 3065, 2925, 2854, 1741, 1649, 1526, 1491, 1379, 1338, 1264, 1240, 1200, 1174, 1070, 711 cm$^{-1}$; $^1$H NMR 8.0–7.95 (m, 2 H), 7.5–7.4 (m, 2 H), 7.33 (bs, 6 H), 6.93 (d, 0.3 H, J=7.0 Hz), 6.85 (d, 0.7 H, J=7.2 Hz), 5.18–5.07 (m, 2 H), 4.65–4.55 (m, 1 H), 3.7–3.3 (m, 4 H), 2.98 (s, 1 H), 2.96 (s, 2 H), 2.71 (d, 3 H, J=2.6 Hz), 2.6–2.0 (m, 6 H), 1.58 (t, 2 H, J=6.8 Hz), 1.3–1.1 (bs, 12 H), 0.86 (t, 3 H, J=6.9 Hz) $^{13}$C NMR δ 173.3, 172.8, 172.0, 171.9, 182.5, 158.6, 153.2, 152.8, 135.9, 130.7, 130.6, 129.7, 128.8, 128.5, 128.3, 128.2, 126.7, 126.5, 126.2, 66.9, 52.2, 52.1, 48.9, 47.6, 37.2, 37.1, 36.4, 36.3, 36.2, 34.1, 31.8, 29.6, 29.5, 29.4, 29.3, 29.2, 28.9, 26.8, 26.6, 25.5, 22.8, 14.1, 11.8; MS (El) m/z (relative intensity) 632 (38), 497 (9), 405 (18), 374 (22), 260 (21), 220 (42), 186 (56), 105 (18), 91 (100); HRMS calculated for C$_{36}$H$_{48}$N$_4$O$_6$: 632.3574, found: 632.3572.

EXAMPLE II

Figure 2:
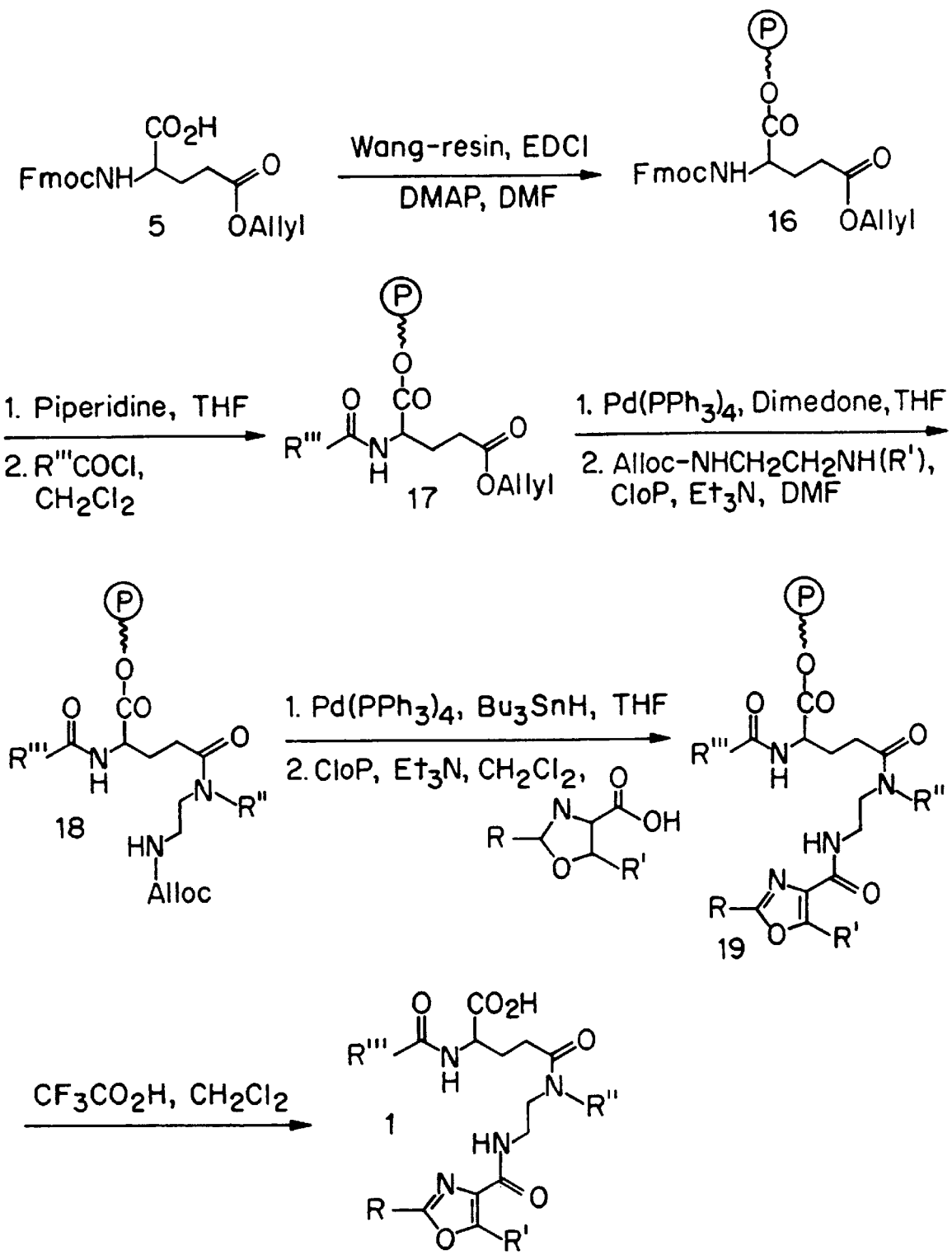
FIG. 2 presents a representative scheme for the synthesis of compounds having formula I.

The solution phase synthesis of compound (formula II) in Example I established the necessary general protocols for the preparation of a library of structural variants of the compounds of formula I on a solid support. Solid phase synthesis of compounds of formula I is depicted in FIG. 2 and proceeded as follows.

Coupling of diprotected glutamate 5 to the polystyrene-based Wang resin described by Wang (1973), *J. Am. Chem. Soc.* 95:1328, with EDCl was performed on large scale and provided a supply of solid phase beads. The base-labile Fmoc protective group was removed by treatment with piperidine and THF, and the resin was distributed to three specially designed Schlenk filters equipped with suction adapters and inert gas inlets for maintaining steady bubbling. After the addition of solvent, hydrophobic residues R'''COCl were added to each flask, which provided three different amide derivatives 17. After filtration and rinsing of the resin, allyl esters 17 were deprotected via Pd(0) chemistry and each batch was distributed over three modified Schlenk filters, providing nine different reaction sites for acylation. Addition of three different N-allyloxycarbonyl protected diamines in the presence of PyBroP[39] or CloP[40] as coupling agents extended the side chain carboxyl terminus of glutamic acid toward the desired heterocyclic moiety in 1. The resulting nine compounds 18 were each deprotected at the N-terminus and distributed over two additional Schlenk filters for the final segment condensation. Coupling with two different oxazole carboxylic acids in the presence of CloP and final purification by rinsing with solvent provided the phosphatase library (formula I) still attached to the solid support. Complete or partial cleavage with 50% trifluoroacidic acid was necessary to release the carboxylate which is required for biological activity. After filtration of the solid support and evaporation of the resulting mother liquor, the desired compounds of formula I were obtained in a chemically pure and structurally well defined fashion ready for rapid throughput biological screening. In each case, the purity of the final compound was >60% according to spectroscopic analysis ($^1$H NMR, MS). The contamination was derived from incomplete couplings to the sterically hindered secondary amine moiety of Alloc-NHCH$_2$CH$_2$NH(R'').

The foregoing synthesis is provided in more detail as follows:

Step 1, 5→16. In a medium porosity Schlenk filter apparatus was placed 750 mg of Wang resin (0.96 mmol/g, 0.72 mmol of active sites). The resin was suspended in 12 mL of dry DMF and a stream of nitrogen was forced up through the filter at a rate which allowed the solvent to gently bubble. To this reaction mixture was added 1.47 g (3.6 mmol) of 5. The suspension was agitated for 5 min and treated with 26 mg (0.216 mmol) of DMAP and 550 mg (2.88 mmol) of EDCl, agitated at 22° C. for 18 h and filtered, and the resin was washed with DMF (2×10 mL), H$_2$O (3×10 mL), THF (3×10 mL), and CH$_2$Cl$_2$ (3×10 mL). The resin was dried under vacuum and the remaining active sites were capped by addition of 10 mL of CH$_2$Cl$_2$ and 10 mL of acetic anhydride along with 26 mg (2.88 mmol) of DMAP to the resin. Bubbling was continued at 22° C. for 3 h and the resin was then washed with CH$_2$Cl$_2$ (6×15 mL) and dried in vacuo. To test the loading on the resin, 30 mg of resin was removed and suspended in 2 mL of trifluoroacetic acid for 5 min at 22° C., filtered and washed (3×3 mL) with CH$_2$Cl$_2$. The filtrate was concentrated in vacuo to give 7.3 mg (85%) of 5.

Step 2, 16→17. A suspension of 690 mg (0.576 mmol) of 2-(9H-fluoren-9-ylmethoxycarbonylamino) pentanedioic acid 5-allyl ester linked to Wang resin 16 in 15 mL of THF was treated with 6 mL (57.6 mmol) of piperidine, agitated by bubbling for 30 min, filtered and washed with CH$_2$Cl$_2$ (6×10 mL). The resin was dried in vacuo. A suspension of this resin in 10 mL of CH$_2$Cl$_2$ was treated with 0.48 mL (2.31 mmol) of decanoyl chloride and 14 mg (0.115 mmol) of DMAP. The reaction mixture was agitated at 22° C. for 6 h, filtered and the resin was washed with CH$_2$C$_2$ (6×10 mL) and dried in vacuo.

Step 3, 17→18. A suspension of 690 mg (0.576 mmol) of 2-decanoylamino-pentanedioic acid 5-allyl ester linked to Wang resin 17 in 10 mL of THF was treated with 67 mg (0.0576 mmol) of tetrakis(triphenylphosphine) palladium (0) and 806 mg (5.75 mmol) of dimedone, and agitated by bubbling at 22° C. for 18 h. The resin was then filtered, washed with THF (2×10 mL), CH$_2$Cl$_2$ (2×10 mL), MeOH (2×10 mL), H$_2$O (2×10 mL), 1% acetic acid solution (2×10 mL), H$_2$O (2×10 mL), MeOH (2×10 mL), CH$_2$Cl$_2$ (2×10 mL), and dried in vacuo. Cleavage and examination of 40 mg of resin by $^1$H NMR showed full deprotection of the allyl ester.

A suspension of this resin in 12 mL of DMF was treated with 0.22 mL (1.572 mmol) of triethylamine and 414.1 mg (2.62 mmol) of Alloc-NHCH$_2$CH$_2$NHMe. After agitating the reaction mixture for 5 min to ensure proper mixing, 540 mg (1.572 mmol) of CloP was added. The reaction mixture was agitated with bubbling for 18 h at 30° C., cooled to 22° C., and the resin was filtered and washed with DMF (2×10 mL), CH$_2$Cl$_2$ (2×10 mL), MeOH (2×10 mL), H$_2$O (2×10 mL), THF (2×10 mL), and CH$_2$Cl$_2$ (2×10 mL). The resin was dried in vacuo and 40 mg of resin was cleaved with CF$_3$CO$_2$H. The $^1$H NMR of the residue showed that coupling had occurred to nearly 100%.

Step 5, 18→19. A suspension of 200 mg (0.192 mmol) of 4-[(2-allyloxycarbonylaminoethyl)-methyl-carbamoyl]-2-decanoylamino-butyric acid linked to Wang resin 18 in 6 mL of CH$_2$Cl$_2$ was treated with 12 mg (0.0096 mmol) of tetrakistriphenylphosphine Pd(0), 62 µl (0.230 mmol) of tributyltin hydride, and 10 µl of H$_2$O. The reaction mixture was agitated with bubbling N$_2$ for 15 min, filtered, and the resin was washed with 10 mL portions of CH$_2$Cl$_2$, THF, acetone, MeOH, H$_2$O, acetone, EtOAc, hexanes, THF, and CH$_2$Cl$_2$. The resin was then dried in vacuo and 15 mg was removed for testing. The $^1$H NMR of the TFA-cleaved residue showed full deprotection as well as full removal of all tin side products.

A suspension of 185 mg (0.190 mmol) of this resin in 8 mL of CH$_2$Cl$_2$ was treated with 117 mg (0.576 mmol) of oxazole carboxylic acid, 198 mg (0.576 mg) of CloP, and 80 µl (0.576 mmol) of triethylamine. The reaction mixture was agitated by bubbling with N$_2$ for 3 h, filtered, and washed with 20 mL of CH$_2$Cl$_2$, acetone, water, acetone, and CH$_2$Cl$_2$. The resin was dried in vacuo and 15 mg was removed for testing. The $^1$H NMR of the residue showed that the reaction had gone to 60% completion. The resin was subsequently submitted to a second coupling cycle.

Step 6, 19→1. A suspension of 115 mg (0.12 mmol) of 2-decanoylamino-4-(methyl-{3-[5-methyl-2-phenyl-oxazole-4-carbonyl]-ethyl}-carbamoyi)-butyric acid linked to Wang resin 19 in 3 mL of TFA was stirred for 5 min, filtered, and washed with 5 mL of CH$_2$Cl$_2$. The extract was concentrated in vacuo to provide 33.1 mg (100% for step 2 to step 6) of 1. A $^1$H NMR showed the product to be 66% pure with 2-acylamino-pentanedioic acid as the major impurity. Acid 1a was dissolved in 3 mL of CH$_2$Cl$_2$ and treated with 0.016 mL (0.138 mmol) of benzyl bromide and 0.02 mL (0.138 mmol) of DBU to provide material identical with the benzyl ester 2 prepared by solution phase chemistry.

EXAMPLE III

The following compounds 1a–r (Table 1) corresponding to formula I were tested for their ability to inhibit PP1, PP2A and PP3.

TABLE 1

| Compound | R | R' | R" | R'" |
| --- | --- | --- | --- | --- |
| 1a | Ph | CH$_3$ | CH$_3$ | n-C$_9$H$_{19}$ |
| 1b | Ph | CH$_3$ | n-C$_6$H$_{13}$ | n-C$_9$H$_{19}$ |
| 1c | Ph | CH$_3$ | Bn | n-C$_9$H$_{19}$ |
| 1d | Ph | Ph | CH$_3$ | n-C$_9$H$_{19}$ |
| 1e | Ph | Ph | n-C$_6$H$_{13}$ | n-C$_9$H$_{19}$ |
| 1f | Ph | Ph | Bn | n-C$_9$H$_{19}$ |
| 1g | Ph | CH$_3$ | CH$_3$ | PhCH$_2$CH$_2$ |
| 1h | Ph | CH$_3$ | n-C$_6$H$_{13}$ | PhCH$_2$CH$_2$ |
| 1i | Ph | CH$_3$ | Bn | PhCH$_2$CH$_2$ |
| 1j | Ph | Ph | CH$_3$ | PhCH$_2$CH$_2$ |
| 1k | Ph | Ph | n-C$_6$H$_{13}$ | PhCH$_2$CH$_2$ |
| 1l | Ph | Ph | Bn | PhCH$_2$CH$_2$ |
| 1m | Ph | CH$_3$ | CH$_3$ | PhCH=CH |
| 1n | Ph | CH$_3$ | n-C$_6$H$_{13}$ | PhCH=CH |
| 1o | Ph | CH$_3$ | Bn | PhCH=CH |
| 1p | Ph | Ph | CH$_3$ | PhCH=CH |
| 1q | Ph | Ph | n-C$_6$H$_{13}$ | PhCH=CH |
| 1r | Ph | Ph | Bn | PhCH=CH |

Phosphatase activity and the inhibitory activity of the compounds of Table 1 were determined by the method of Honkanen et al. (1994) *Toxicon* 32:339. Briefly, phosphatase activity against phosphorylase-a or phosphohistone was determined by the quantification of liberated [$^{32}$P]. Assays, 80 µl total volume, containing 50 mM Tris-HCl, pH 7.4, 0.5 mM DTT, 1 mM EDTA (assay buffer) and [$^{32}$P] phosphoprotein (1–2 µM PO$_4$), were conducted as described previously (Honkanen et al., 1991 *Mol. Pharmac.* 40:577). Dephosphorylation reactions were routinely conducted for 5–10 min. using phosphorylase-a as a substrate and for 10–20 min. using phosphohistone. In all assays the dephosphorylation of substrate was kept to less than 10% of the total phosphorylated substrate available, and the reactions were adjusted to ensure that enzyme activity was linear with respect to enzyme concentration and time. [$^{32}$P] Phosphate liberated by the enzymes was extracted as a phosphomolybdate complex and measured according to the methods of Killilea et al. (1978) *Arch. Biochem. Biophys.* 191.638. Inhibition of protein phosphatase activity by inhibitors was determined by adding the 100 µM of inhibitors to the enzyme mixture 5–10 min. prior to initiating the reaction with the addition of substrate.

Results are presented in Table 2 as the percent inhibition relative to control (100%).

TABLE 2

| Compound | PP1 | PP2A | PP3 |
|---|---|---|---|
| none | 100 | 100 | 100 |
| 1a | 121 | 100 | 76 |
| 1b | 59 | 135 | 32 |
| 1c | ND | 129 | 28 |
| 1d | 53 | 69 | 33 |
| 1e | 153 | 152 | 71 |
| 1f | 117 | 156 | 85 |
| 1g | 53 | 109 | 21 |
| 1h | 63 | 88 | 17 |
| 1i | ND | 80 | 14 |
| 1j | 80 | 72 | 38 |
| 1k | 48 | 67 | 24 |
| 1L | 59 | 69 | 22 |
| 1m | 111 | 108 | 60 |
| 1n | 40 | 87 | 26 |
| 1o | 64 | 88 | 13 |
| 1p | 65 | 99 | 68 |
| 1q | 85 | 60 | 28 |
| 1r | 53 | 68 | 15 |

TABLE 3

| Compound | CDC25A | CDC25B |
|---|---|---|
| none | 100 | 100 |
| 1a | 67 | 106 |
| 1b | 14 | 44 |
| 1c | 11 | 42 |
| 1d | 99 | 91 |
| 1e | 7 | 17 |
| 1f | 3 | 15 |
| 1g | 50 | 81 |
| 1h | 36 | 69 |
| 1i | 31 | 63 |
| 1j | 107 | 90 |
| 1k | 83 | 76 |
| 1L | 62 | 69 |
| 1m | 19 | 45 |
| 1n | 29 | 66 |
| 1o | 35 | 66 |
| 1p | 71 | 87 |
| 1q | 55 | 62 |
| 1r | 42 | 56 |

Compound 1d (R=Ph, R'=Ph, R"=$CH_3$, R'"=n-$C_9H_{19}$) was further assessed for its ability to inhibit PP2A, and compared to calyculin A, a known inhibitor of PP2A.

The activity of the catalytic subunit of bovine cardiac muscle PP2A (Gibco-BRL, Gaithersburg, Md.) was measured with fluorescein diphosphate (Molecular Probes, Inc., Eugene, OR) as a substrate in 96-well microtiter plates. The final incubation mixture (150 µL) composed 25 mM Tris (pH=7.5), 5 mM EDTA, 33 µg/mL BSA, and 20 µM fluorescein diphosphate. Inhibitors were resuspended in DMSO, which was also used as the vehicle control. Reactions were initiated by adding 0.2 units of PP2A and incubated at room temperature overnight. Fluorescence emission from the product was measured with Perseptive Biosystems Cytoflour II (exciton filter, 485 nm; emission filter, 530 nm) (Framingham, Mass.).

Figure 6:
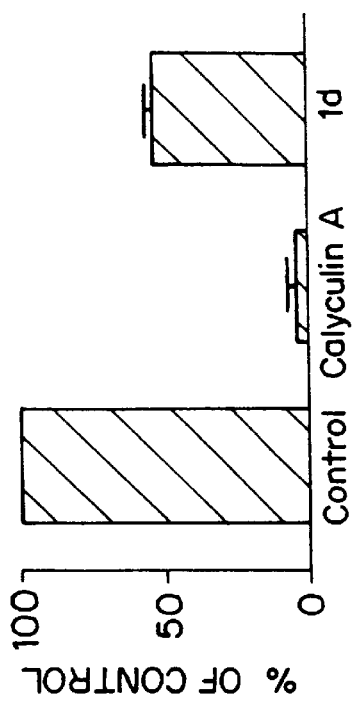
FIG. 6 is a graph of inhibition of PP2A activity by compound 1d. The catalytic subunit of PP2A was incubated with vehicle alone (control), calyculin A (10 nM) or compound 1d (100 uM), and the dephosphorylation of the substrate fluorescein diphosphate determined spectrophotometrically. Mean results of two independent experiments are shown; bars indicate the range.

As demonstrated in FIG. 6, calyculin A inhibited PP2A activity at 10 nM, and compound id caused 50% inhibition at 100 µM.

EXAMPLE IV

Compounds 1a–1r were assessed for ability to inhibit CDC25A and CDC25B activity. Recombinant human CDC25A and CDC25B were obtained as a glutahione-S-transferase (GST) fusion protein using human cDNA and standard molecular biological methods. The cDNA constructs are in a plasmid that is expressed in E. coli under the control of isopropyl-beta-D-thiogalactosidase (IPTG). The bacterial pellet was disrupted by sonication, and centrifuged at 10,000×g. Using glutathione-agarose beads, the fusion protein was purified from postmicrosomal supernant fraction as described by Baratte et al.(1992) Anticancer Res. 12: 873–880. Phosphatase activity was assayed with a spectrofluorimeter under the following conditions: 1 unit (1 U=amount of protein that induces 33 fluoresence units/minute of product) of fusion protein in a final incubation mixture (150 µL) comprised of 25 mM Tris (pH=8.0), 5 mM EDTA, 33 µg/ml BSA, and 20 µM fluorescein diphosphate in 96-well microtiter plates. Plates were preincubated for 1 hour with 0 (control), 0.3, 1, 3, 10, 30, 100 µM compounds at room temperature. After the 1 hour incubation at room temperature, fluorescence of the fluorescein product (Ex. 485 nm; Em. 530 nm) were measured with a Biosystems Cytofluor II (Framingham, Mass.).

Figure 7:
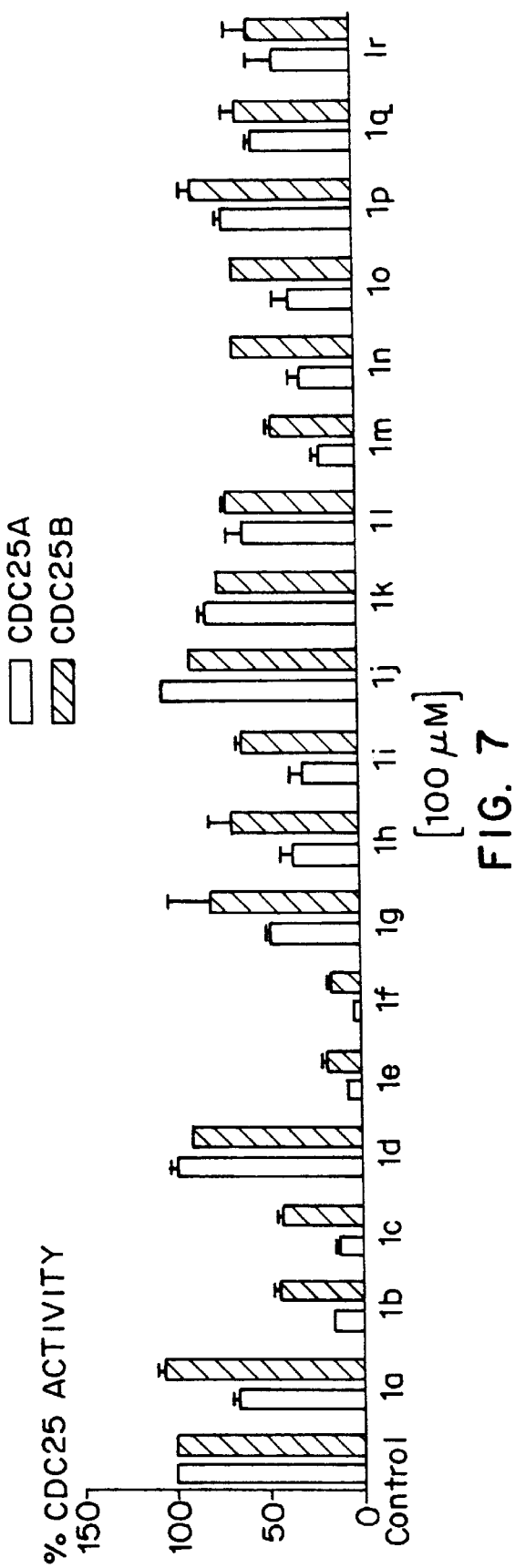
FIG. 7 presents a graph depicting the ability of compounds 1a–r to inhibit CDC25A and CDC25B activity. Results are presented as percentage of control (100%).
Figure 8:
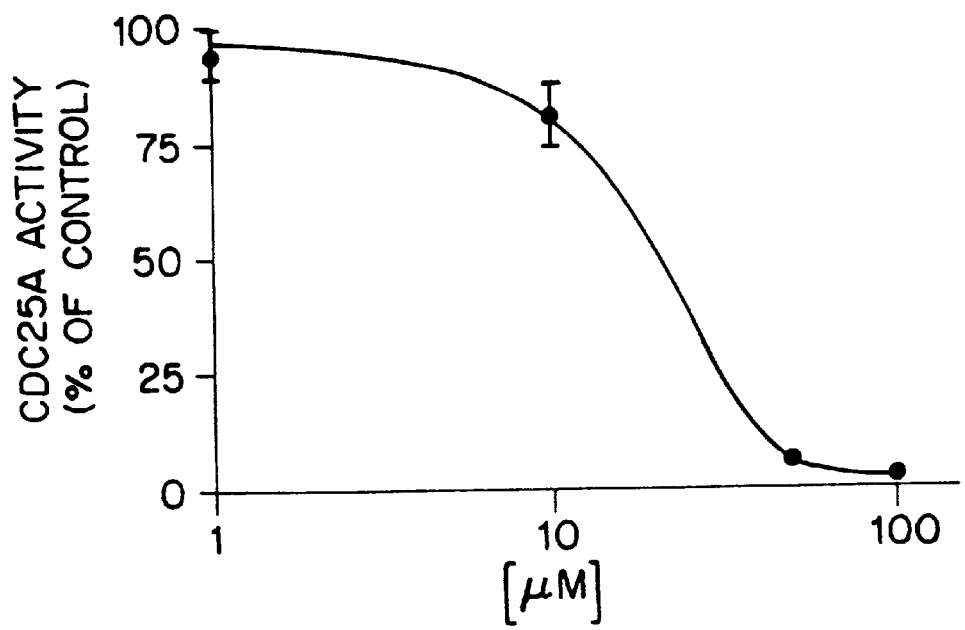
FIG. 8 presents a dose-response curve of the ability of compound if to inhibit CDC25A.

Results are presented in FIG. 7 and Table 3 as percent inhibition relative to control. A dose-response curve for compound 1f is presented in FIG. 8.

The foregoing results demonstrate that compounds 1a–1c and 1e–1r are capable of inhibiting the activity of CDC25A and/or CDC25B.

EXAMPLE V

Compounds 1a–1r were tested for antiproliferative activity against human MDA-MB-231 breast cancer cells.

Human MDA-MB-231 breast carcinoma cells were obtained from the American Type Culture Collection at passage 28 and were maintained for no longer than 20 passages. The cells were grown in RPMI-1640 supplemented with 1% penicillin (100 µg/mL) and streptomycin (100 µg/mL), 1% L-glutamate, and 10% fetal bovine serum in a humidified incubator at 37° C. under 5% $CO_2$ in air. Cells were routinely found free of mycoplasma. To remove cells from the monolayer for passage or flow cytometry, cells were washed two times with phosphate buffer and briefly (<3 min) treated with 0.05% trypsin/2 mM EDTA at room temperature. After the addition of at least two volumes of growth medium containing 10% fetal bovine serum, the cells were centrifuged at 1,000×g for 5 min. Compounds were made into stock solutions using DMSO, and stored at −20° C. All compounds and controls were added to obtain a final concentration of 0.1–0.2% (v/v) of the final solution for experiments.

The antiproliferative activity of the compounds was determined by the method of Lazo et al. (1995) J. Biol. Chem. 270:5506. Briefly, cells (6.5×10³ cells/cm²) were plated in 96 well flat bottom plates for the cytotoxicity studies and incubated at 37° C. for 48 h. The plating medium was aspirated off 96 well plates and 200 µL of growth medium containing the compound was added per well. Compounds were used at from 0 to the highest available concentration which ranged from 30 to 100 µM. Plates were incubated for 72 h, and then washed 4× with serum free medium. After washing, 50 µL of 3-[4,5-dimethylthiazol-2-yl]-2,5-diphenyl tetrazolium bromide solution (2 mg/mL) was added to each well, followed by 150 µL of complete growth medium. Plates were then incubated an additional 4 h at 37° C. The solution was aspirated off, 200 µL of DMSO added, and the plates were shaken for 30 min at room temperature. Absorbance at 540 nm was determined with a Titertek Multiskan Plus plate reader. Biologically active compounds were tested at least 3 independent times.

Figure 9:
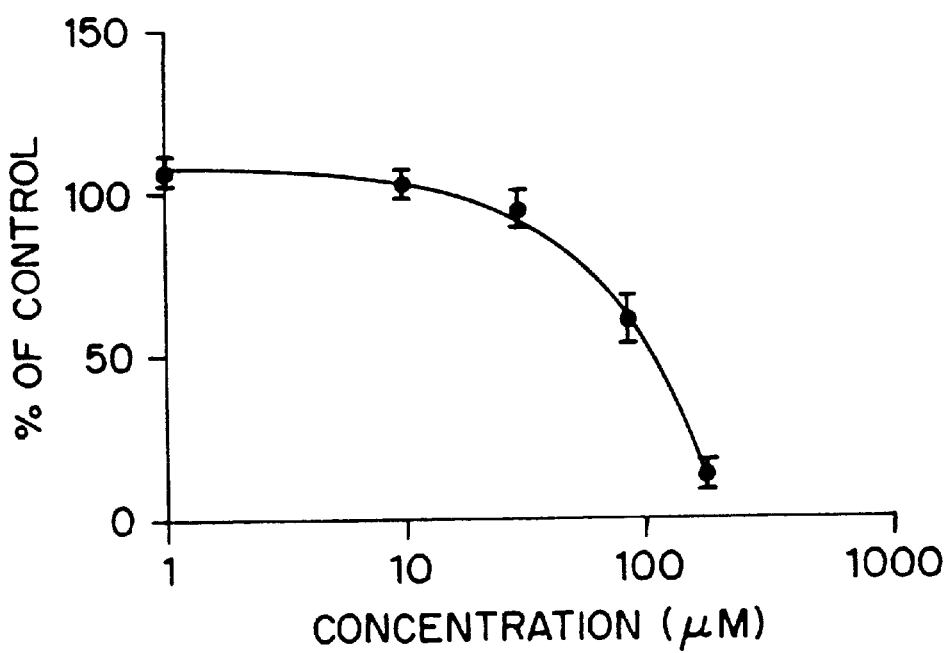
FIG. 9 is a graph showing the anti-proliferative effect of compound if against human MDA-MB-231 breast cancer cells.

Administration of compound 1h caused 50% growth inhibition at 20 µM but had no further cytotoxicity at higher drug concentrations. Compound if caused 50% growth inhibition at 100 μM and had a clear concentration-dependency (FIG. 9).

EXAMPLE VI

The cell cycle distribution of human breast cancer cells after treatment with compound if was determined by flow cytometry.

MDA-MB-231 cells ($6.5 \times 10^5/cm^2$) were plated and incubated at 37° C. for 48 h. The plating medium was then aspirated off, and medium containing a concentration of compound if that caused approximately 50% growth inhibition (88–100 μM) was added for 48 to 72 h. Untreated cells at a similar cell density were used as control populations. Single cell preparations were fixed in ice-cold 1% paraformaldehyde, centrifuged at 1,000×g for 5 min, resuspended in Puck's saline, centrifuged, and resuspended in ice-cold 70% ethanol overnight. The cells were removed from fixatives by centrifugation (1,000×g for 5 min) and stained with a 5 μg/mL propidium iodide and 50 μg/mL RNase A solution. Flow cytometry analyses were conducted with a Becton Dickinson FACS Star. Single parameter DNA histograms were collected for 10,000 cells, and cell cycle kinetic parameters calculated using DNA cell cycle analysis software version C (Becton Dickinson). Experiments at 72 h were performed at least 3 independent times.

Results are presented in FIGS. 10A–D.

Exponentially growing human MDA-MB-231 breast cancer cell populations (population doubling time of approximately 30–35 h) typically have approximately 30% of all cells in the S or DNA synthetic phase of the cell cycle (FIGS. 10A and C). In contrast, when MDA-MB-231 cells were incubated for 48 h with 88 μM compound if, there was prominent accumulation in the G1 phase with a concomitant decrease in both S and G2/M phases (FIGS. 10B and C). Incubation of MDA-MB-231 cells for 72 h with 88 μM if also caused a prominent accumulation in the G1 phase (FIG. 10D).

These results demonstrate that compound 1f exhibits a concentration-dependent inhibition in proliferation of MDA-MB-231 cells, and that blockage in cell cycle progression is at the G1 checkpoint.

We claim:

1. A method of inhibiting a protein phosphatase comprising contacting the protein phosphatase with a protein phosphatase-inhibiting effective amount of a compound having the formula

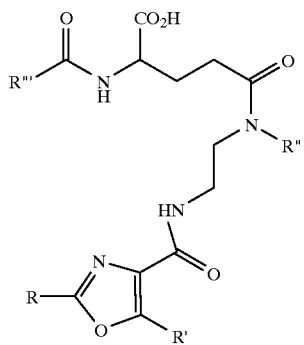

wherein R, R', R", and R'" are independently H, alkyl, alkenyl, alkynyl, cycloalkyl, phenyl, oxetanyl, azetidinyl, furanyl, pyrrole, indolyl, oxazolyl, isoxazolyl, imidazolyl, pyrazolyl, triazolyl, tetrazolyl, pyranyl, pyridyl, pyridonyl, piperidyl, piperazinyl, quinolyl, azepinyl, and diazepinyl.

2. The method of claim 1 wherein said protein phosphatase is a serine/threonine protein phosphatase.

3. The method of claim 2 wherein said protein phosphatase is PP1, PP2A, or PP3.

4. The method of claim 1 wherein said protein phosphatase is a dual specificity phosphatase.

5. The method of claim 4 wherein said phosphatase is CDC25A or CDC25B.

* * * * *

UNITED STATES PATENT AND TRADEMARK OFFICE
CERTIFICATE OF CORRECTION

PATENT NO. : 5,925,660

DATED : JULY 20, 1999

INVENTOR(S) : LAZO ET AL.

It is certified that error appears in the above-identified patent and that said Letters Patent is hereby corrected as shown below:

Column 2, line 3: "trations$_{50}$" should read --tration$_{50}$;
    line 18: "acetate" should be deleted.

Column 3, line 13: "cell," should read --cells,--.

Column 4, lines 49, 51, 55, 59, 64, and 66: "if" should read --1f--.

Column 5, lines 1 and 4: "if." should read --1f.--.

Column 15, line 20: "thiosuffate" should read --thiosulfate--.

Column 16, line 5: "-C" should read --$^{13}$C--.

UNITED STATES PATENT AND TRADEMARK OFFICE
CERTIFICATE OF CORRECTION

PATENT NO. : 5,925,660
DATED : July 20, 1999
INVENTOR(S) : Lazo et al.

It is certified that error appears in the above-identified patent and that said Letters Patent is hereby corrected as shown below:

Column 19, line 45: "glutahione-S-" should read --glutathione-S- --.

Column 19, line 54: "luorimeter" should read --luorometer--.

Column 21, lines 1, 12, 34 and 37: "if" should read --1f--.

Column 22, line 29, claim 1: "and" should read --or--.

Signed and Sealed this

Twelfth Day of December, 2000

Attest:

Attesting Officer

Q. TODD DICKINSON
Director of Patents and Trademarks